US012559776B2

(12) United States Patent
Kim et al.

(10) Patent No.: US 12,559,776 B2
(45) Date of Patent: Feb. 24, 2026

(54) CHEMICAL AND BIOLOGICAL INTEGRATED DEGRADATION PROCESS FOR POLYETHYLENE TEREPHTHALATE (PET), FOR RECYCLING PET

(71) Applicant: Korea University Research and Business Foundation, Seoul (KR)

(72) Inventors: Kyoung Heon Kim, Seoul (KR); Dong Hyun Kim, Seoul (KR); Dong Oh Han, Seoul (KR); Jae Kyun Kim, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 361 days.

(21) Appl. No.: 18/278,976

(22) PCT Filed: Feb. 25, 2022

(86) PCT No.: PCT/KR2022/002784
§ 371 (c)(1),
(2) Date: Aug. 25, 2023

(87) PCT Pub. No.: WO2022/182196
PCT Pub. Date: Sep. 1, 2022

(65) Prior Publication Data
US 2024/0132922 A1 Apr. 25, 2024
US 2024/0229084 A9 Jul. 11, 2024

(30) Foreign Application Priority Data
Feb. 26, 2021 (KR) ........................ 10-2021-0026729

(51) Int. Cl.
*C12P 7/42* (2006.01)
*C07C 67/297* (2006.01)
(52) U.S. Cl.
CPC .............. *C12P 7/42* (2013.01); *C07C 67/297* (2013.01)

(58) Field of Classification Search
CPC ................ C12P 7/40; C12P 7/42; C08J 11/20
See application file for complete search history.

(56) References Cited

U.S. PATENT DOCUMENTS 10,508,186 B2 12/2019 Parrott
2020/0048621 A1 2/2020 Kim

FOREIGN PATENT DOCUMENTS

| KR | 10-2020-0067665 A | 6/2020 |
|---|---|---|
| KR | 10-2020-0119213 A | 10/2020 |
| WO | 2018/168679 A1 | 9/2018 |
| WO | 2019/053392 A1 | 3/2019 |

OTHER PUBLICATIONS

Office Action issued Apr. 18, 2024 in Korean Application No. 10-2022-0025037.
Jian Sun, et al., "Solubilization and Upgrading of High Polyethylene Terephthalate Loadings in a Low-Costing Bifunctional Ionic Liquid", ChemSusChem, 2018, vol. 11, pp. 781-792 (12 pages total).
Brandon C.Knott et al., "Characterization and engineering of a two-enzyme system for plastics depolymerization", Proceedings of the National Academy of Sciences, Oct. 13, 2020, pp. 25476-25485, vol. 117, No. 41.
Dong Hyun Kim et al., "One-Pot Chemo-bioprocess of PET Depolymerization and Recycling Enabled by a Biocompatible Catalyst, Betaine", American Chamical Society Catalysis, Nov. 2021, pp. 3996-4008.
International Search Report for PCT/KR2022/002784 dated Jun. 9, 2022.

*Primary Examiner* — Tekchand Saidha
(74) *Attorney, Agent, or Firm* — Sughrue Mion, PLLC

(57) ABSTRACT

The present invention relates to a chemical and biological integrated degradation process for PET, for recycling PET, and, more specifically, the present invention provides a PET upcycling technique for producing a high-value product via a chemical pretreatment process of PET, a TPA and EG production process using an enzyme, and a process for converting TPA and EG to PCA and GLA, respectively.

8 Claims, 15 Drawing Sheets

Specification includes a Sequence Listing.

[Fig 1]

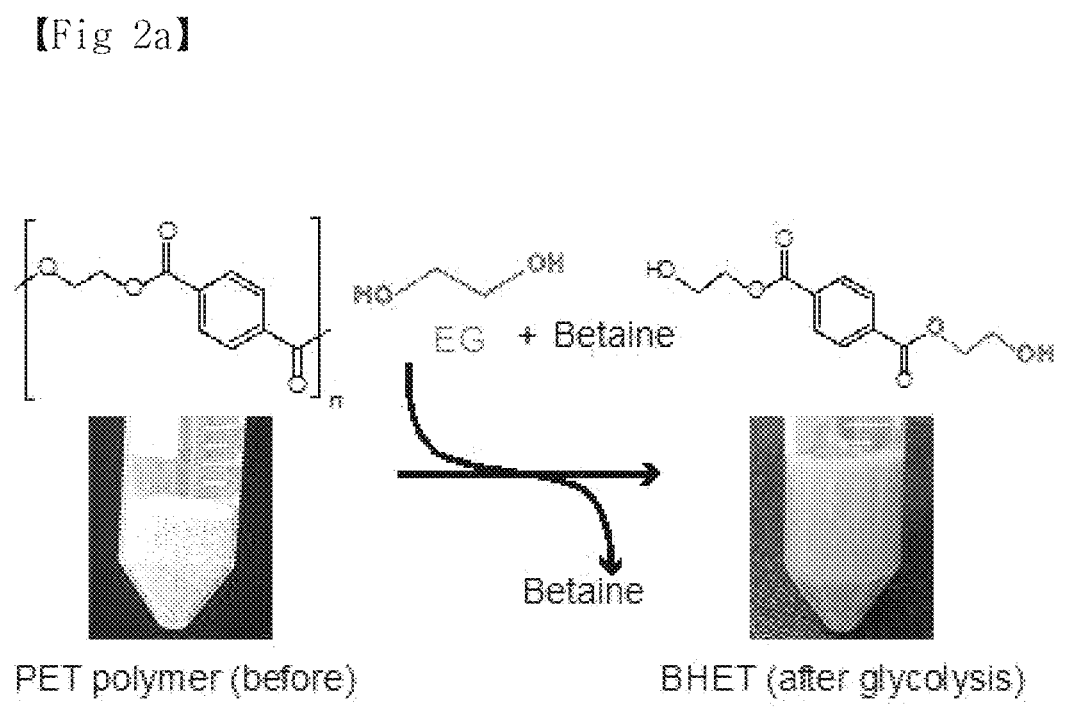

【Fig 2a】

EG  +  Betaine

Betaine

PET polymer (before)                   BHET (after glycolysis)

【Fig 2b】
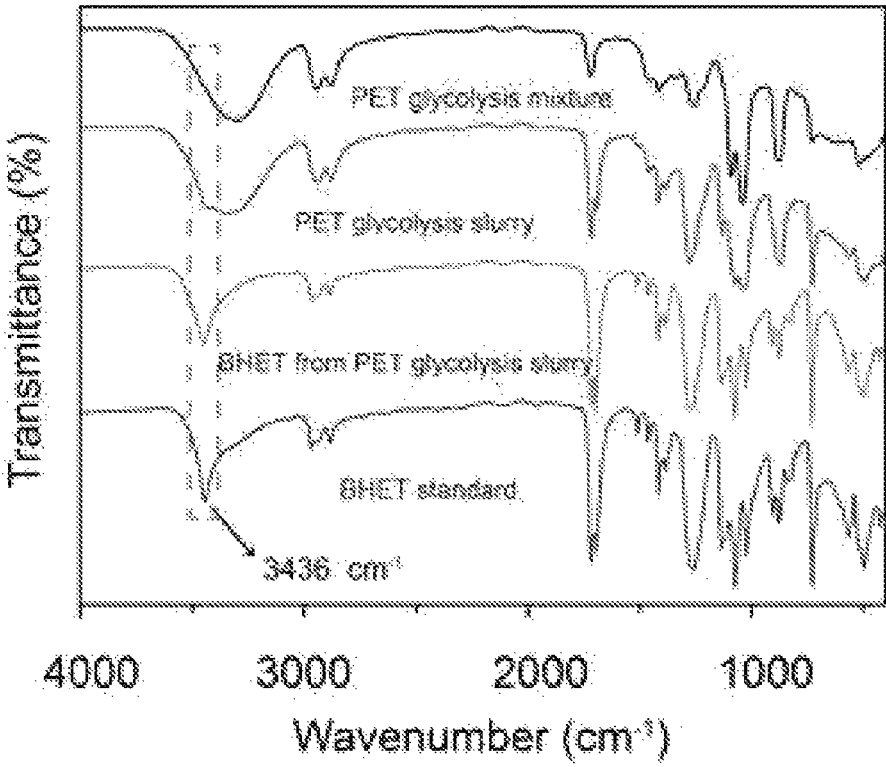
【Fig 2c】
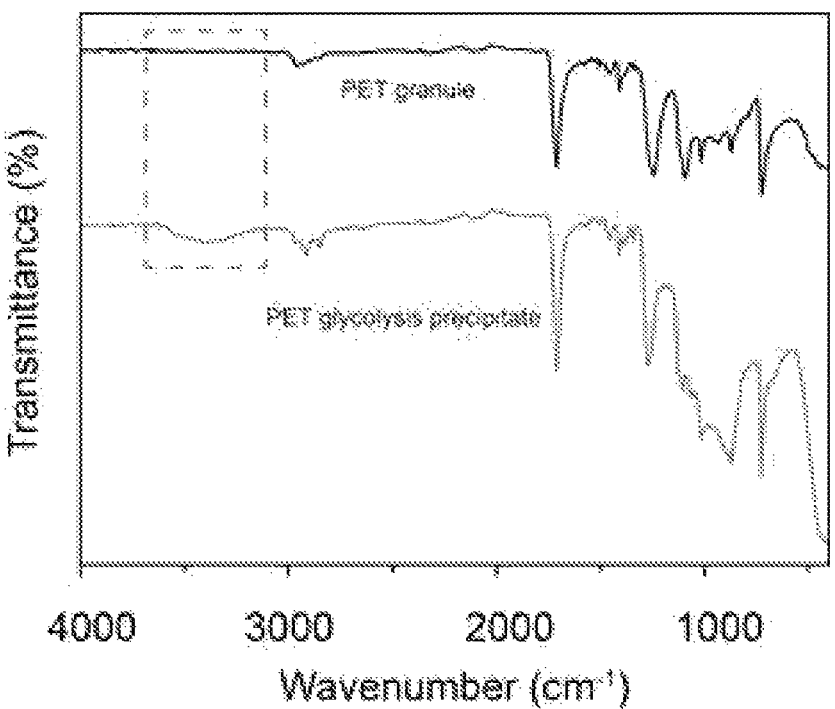

【Fig 2d】
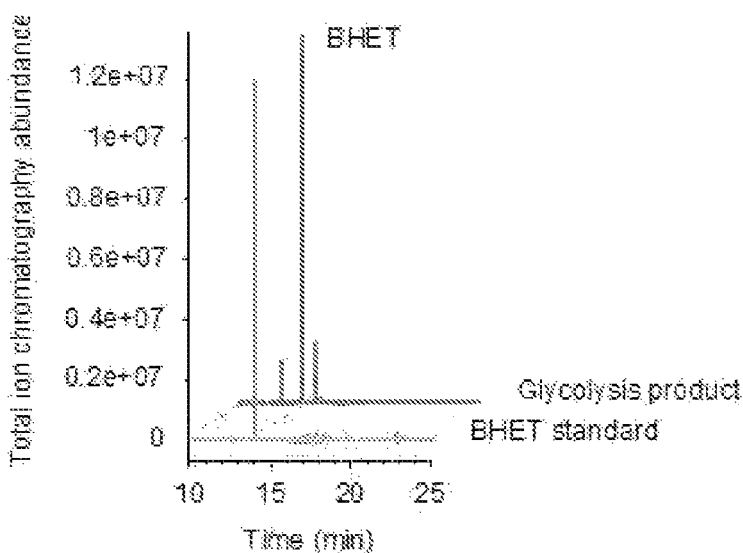
【Fig 2e】
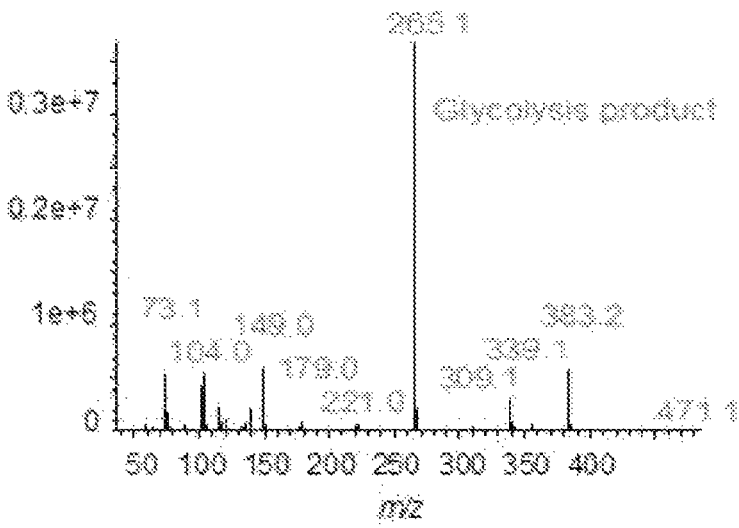

【Fig 2f】
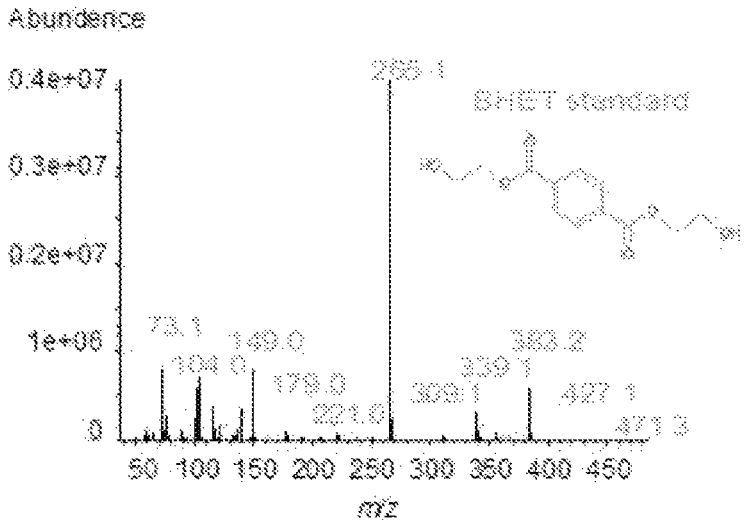
【Fig 2g】
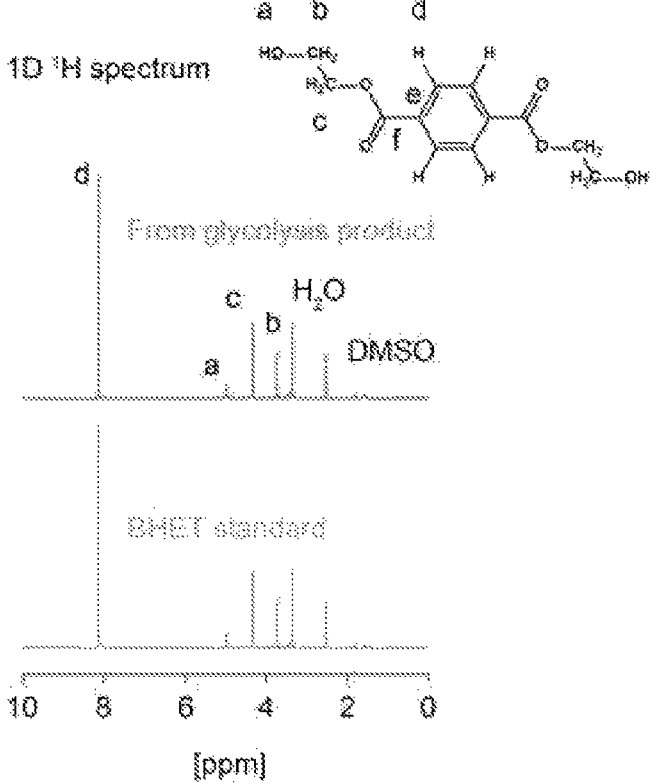

【Fig 2h】
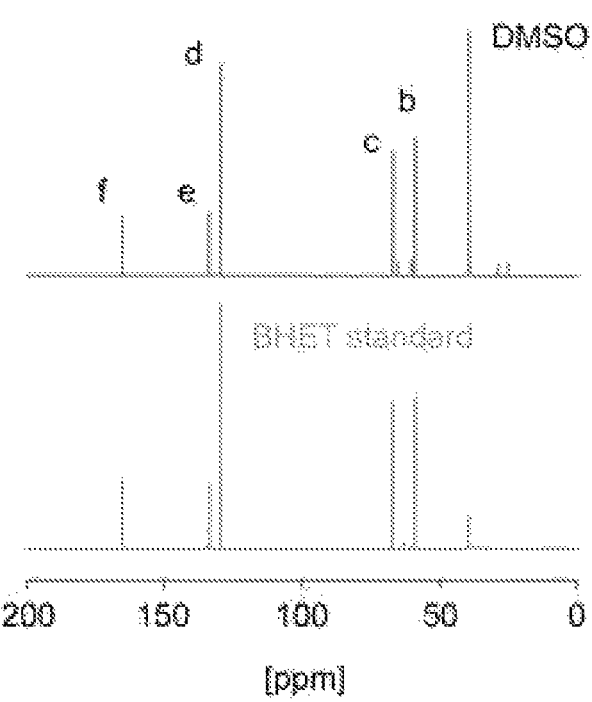

【Fig 3】
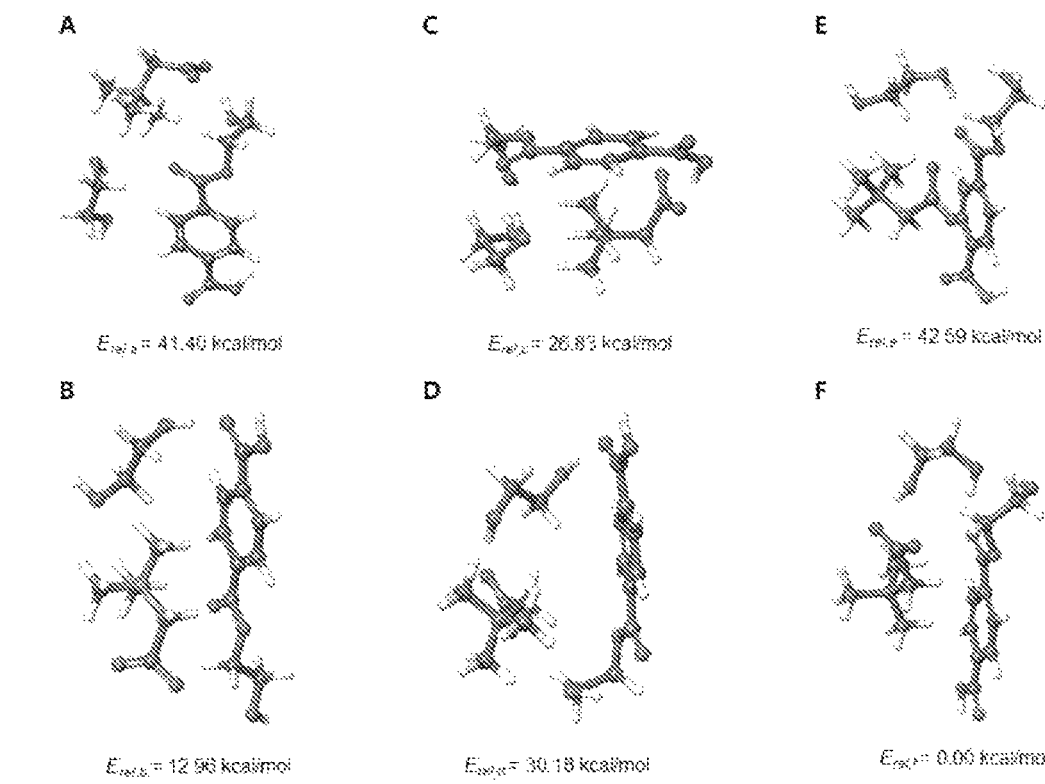
【Fig 4】
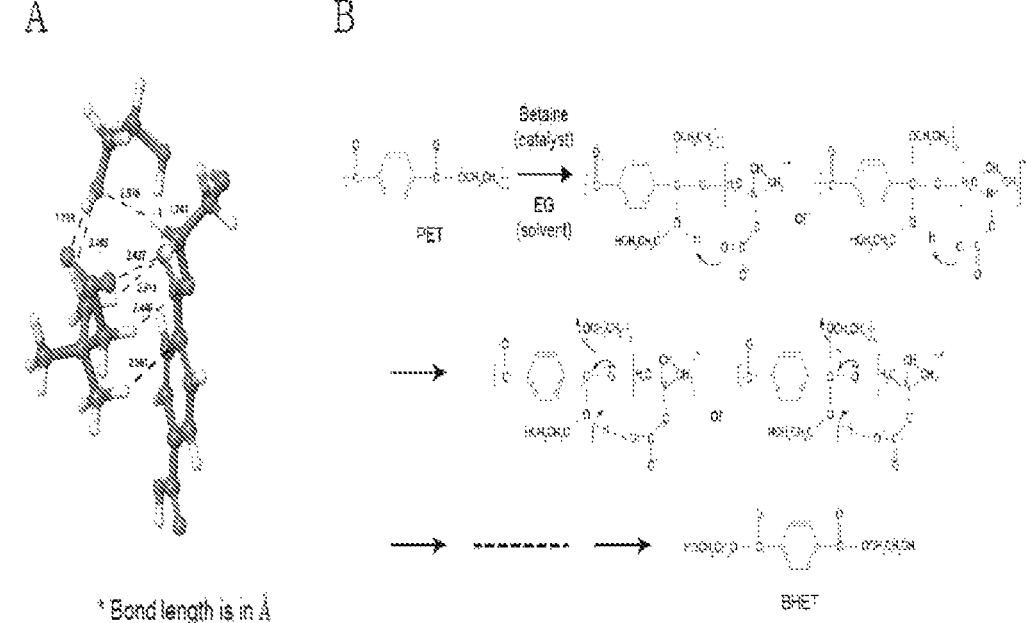

【Fig 5】
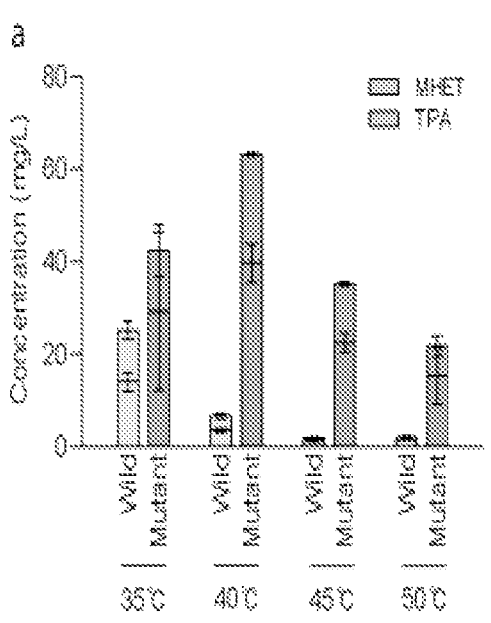 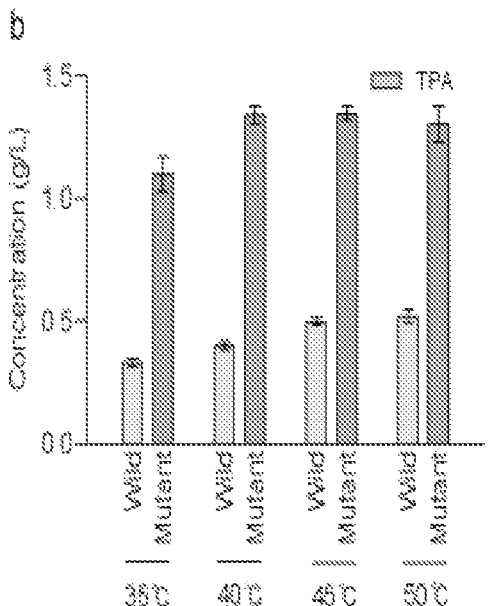
【Fig 6a】
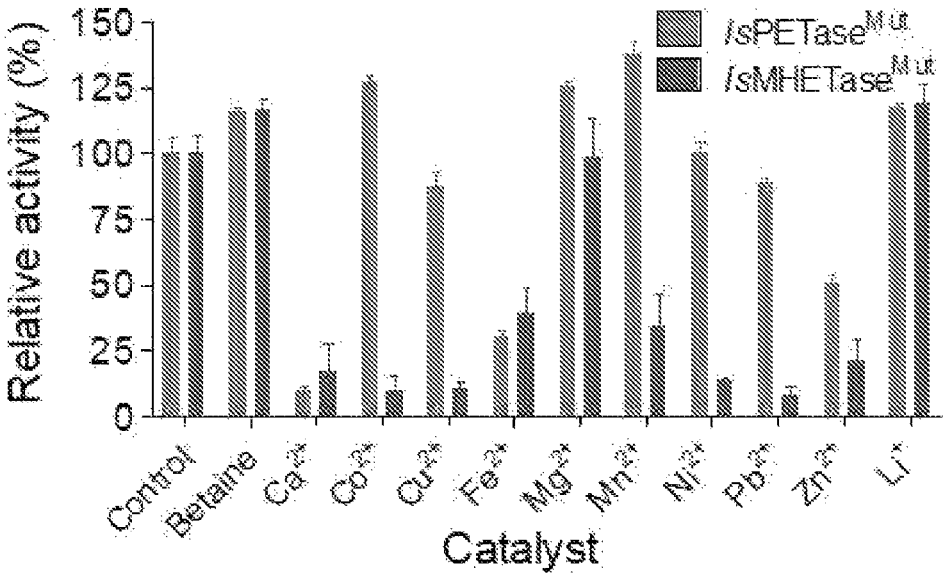

【Fig 6b】
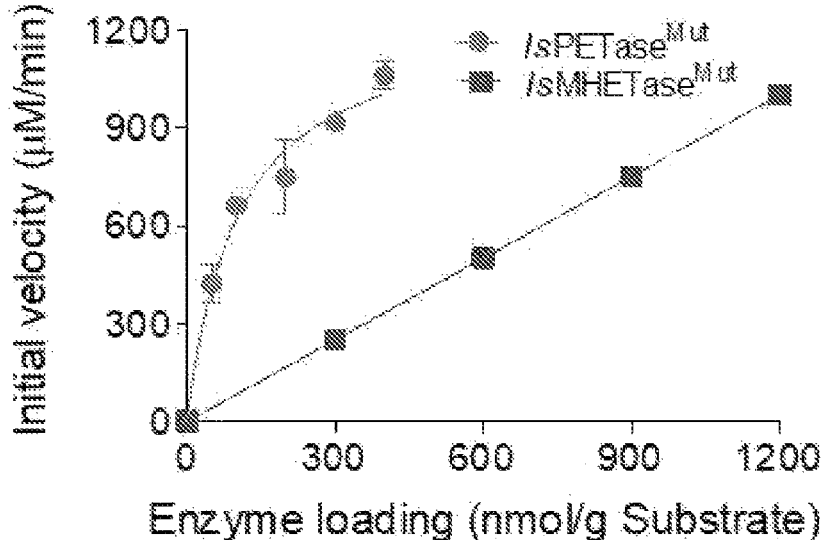
【Fig 6c】
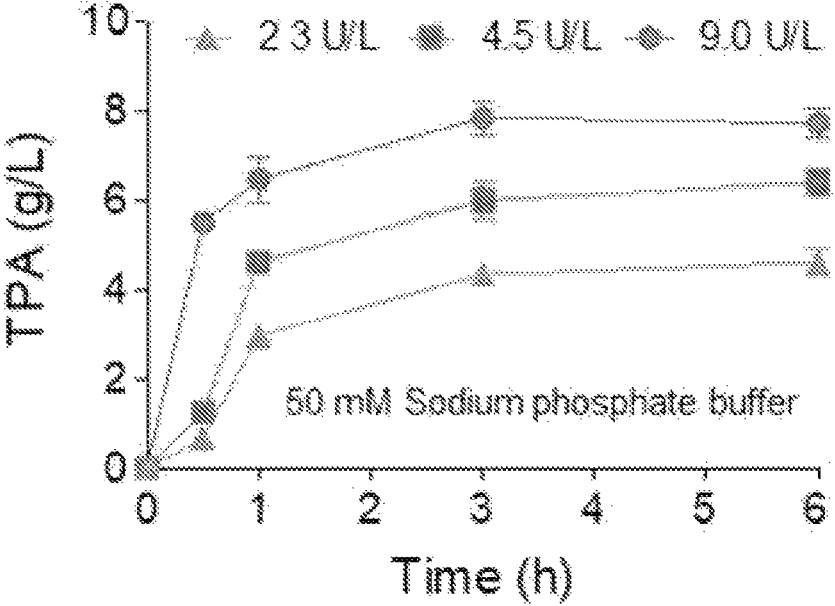

【Fig 6d】
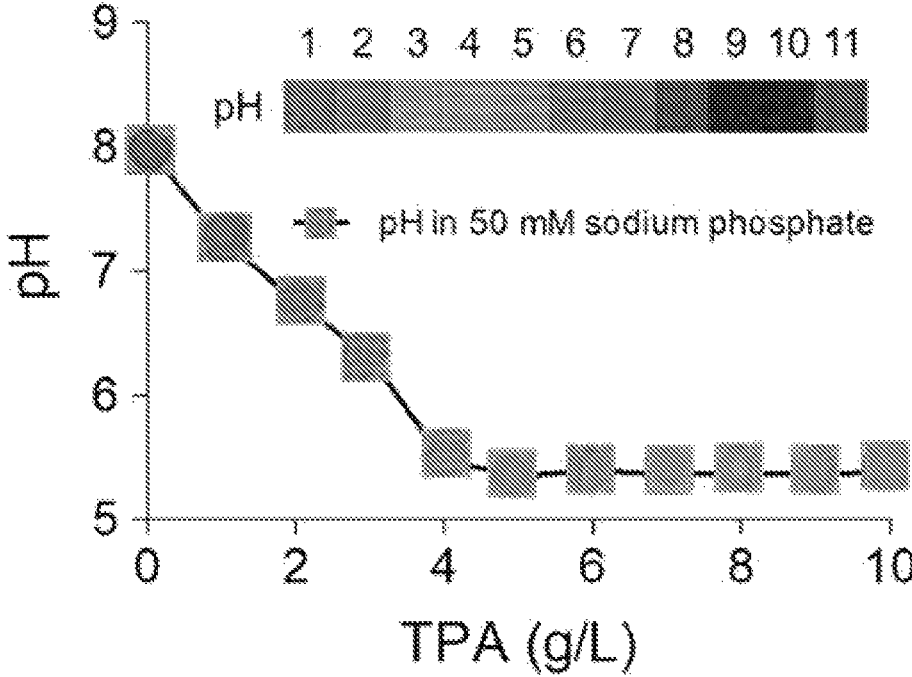
【Fig 6e】
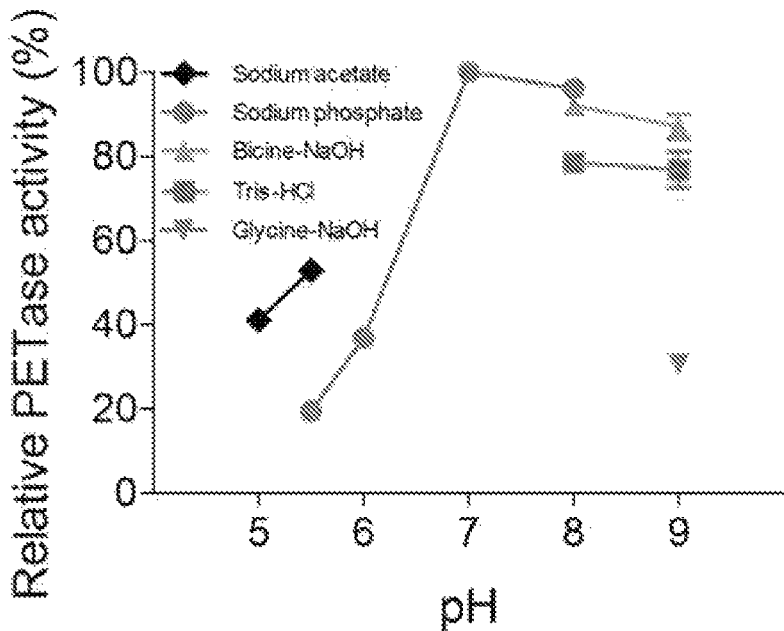

【Fig 6f】
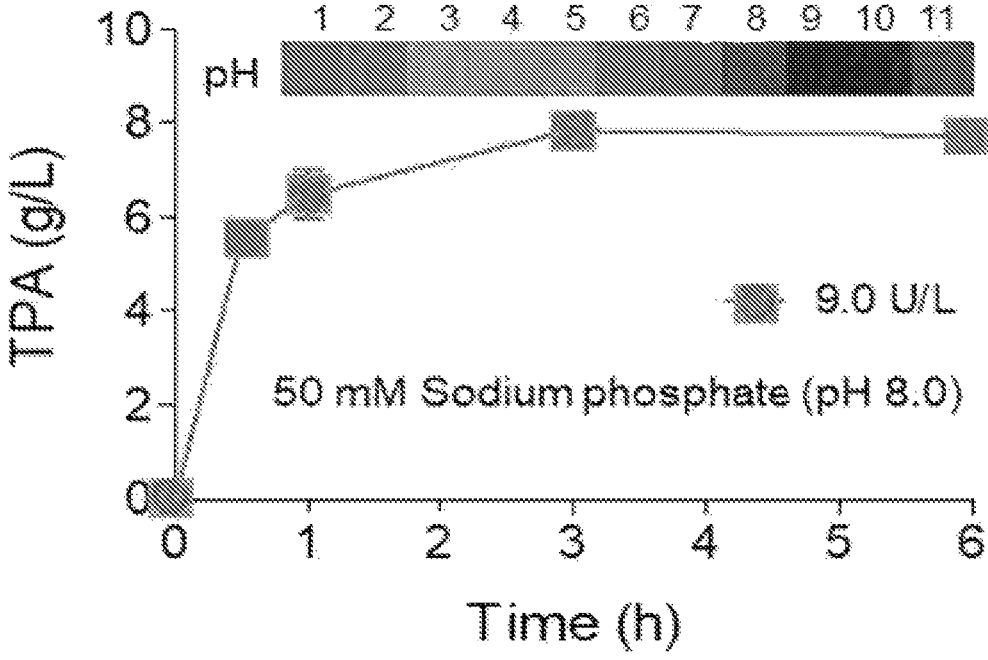
【Fig 6g】
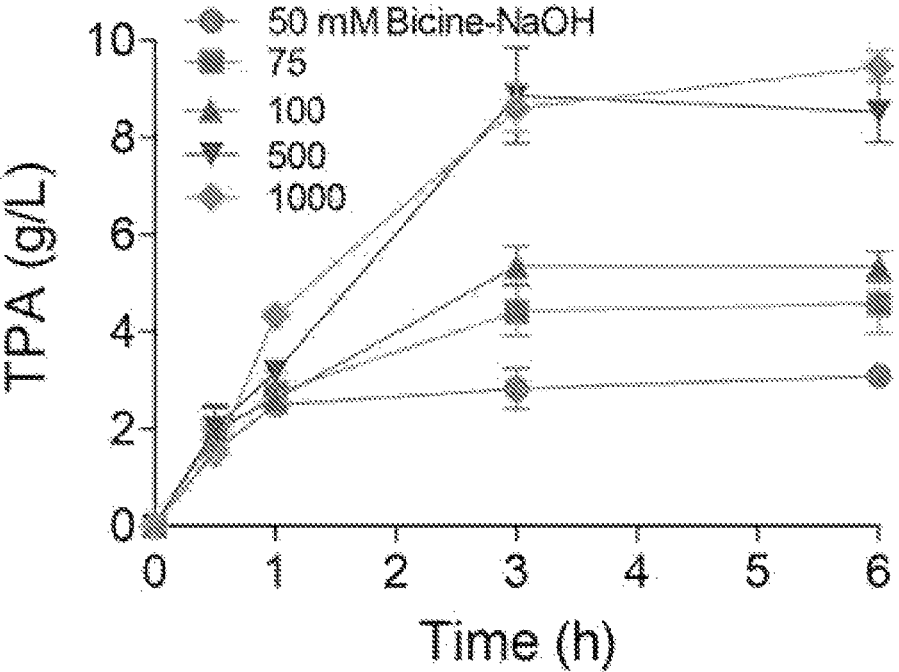

【Fig 6h】
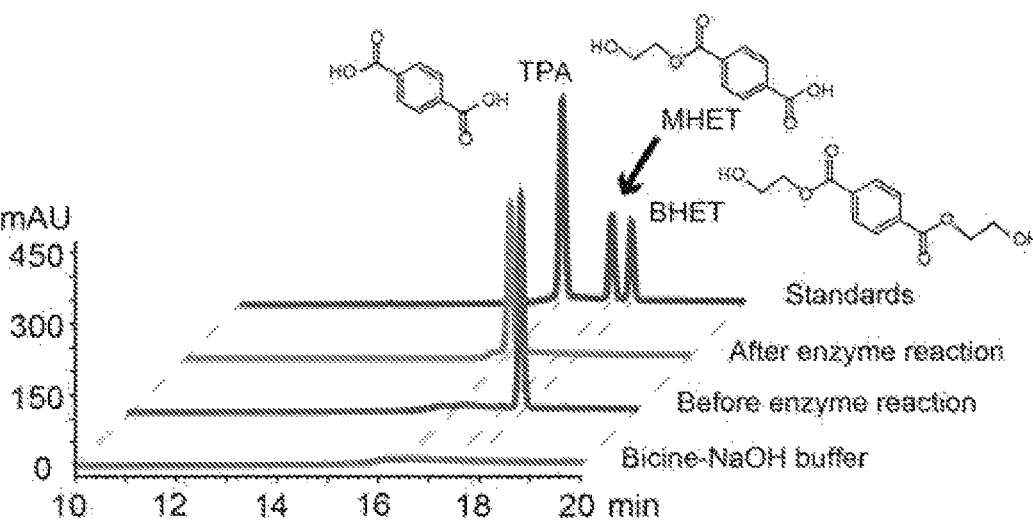
【Fig 6i】
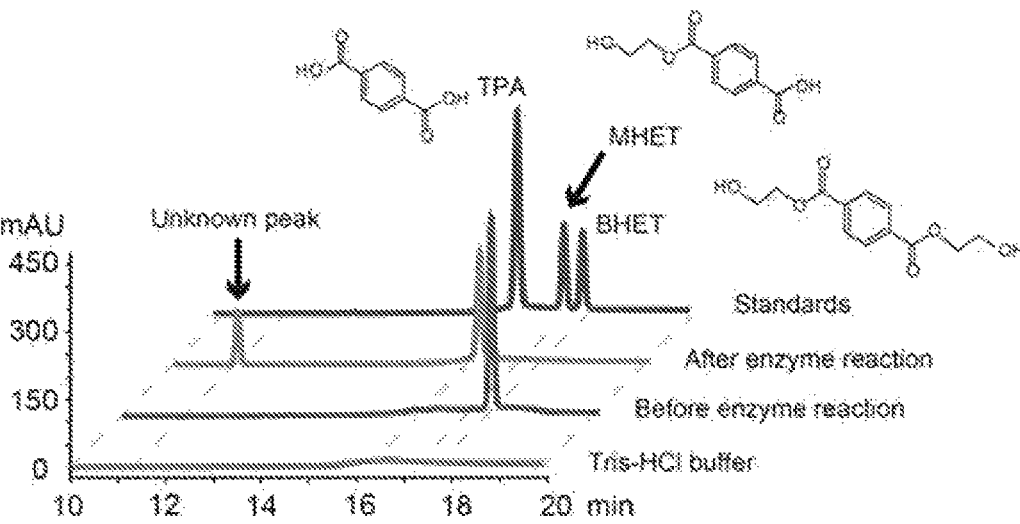

【Fig 6j】
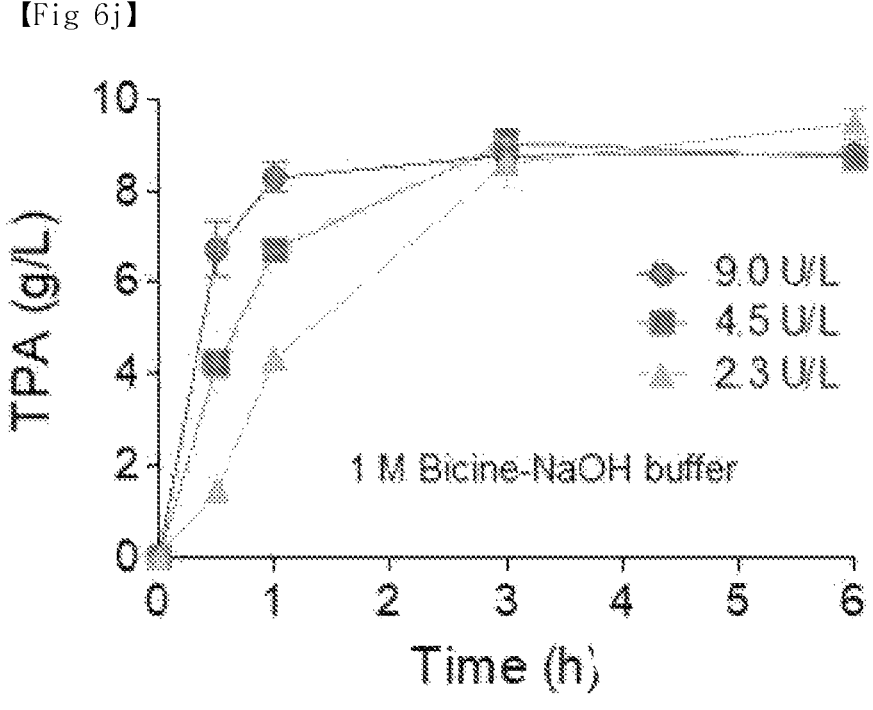
【Fig 6k】

【Fig 6l】
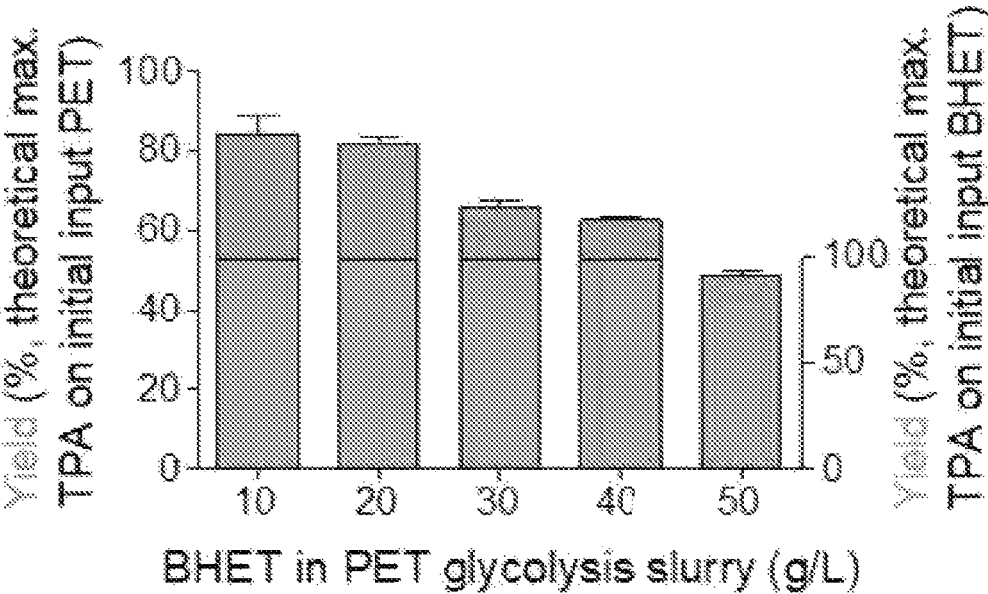
【Fig 6m】
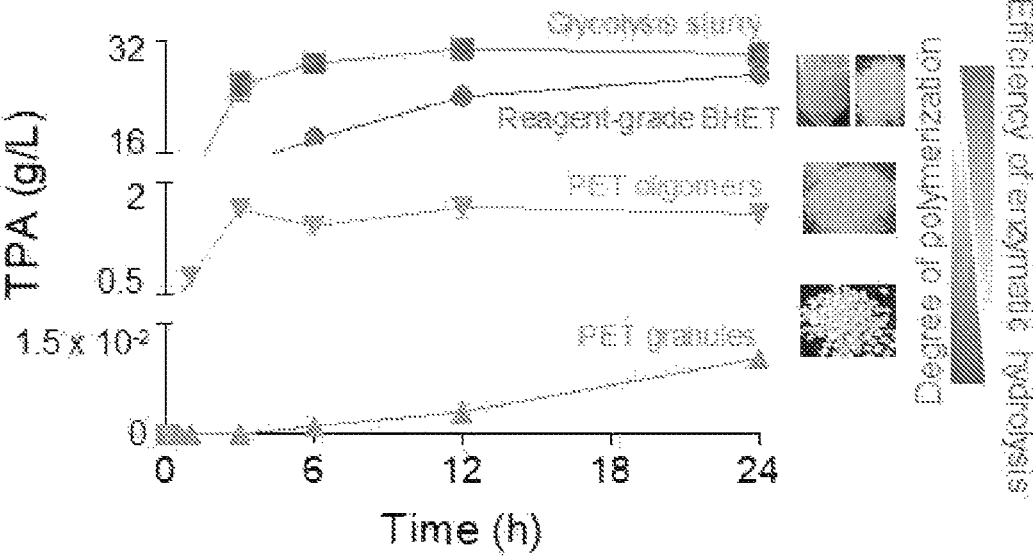

【Fig 7】
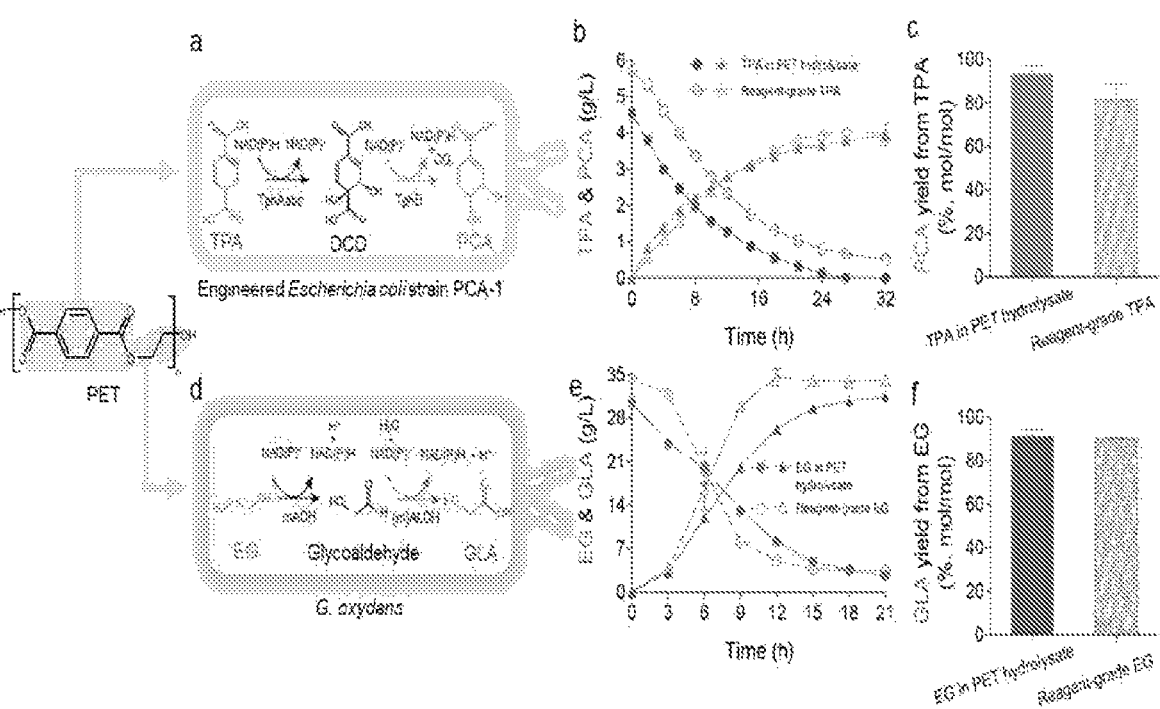

SEQUENCE LISTING

<160> NUMBER OF SEQ ID NOS: 4

<210> SEQ ID NO 1
<211> LENGTH: 804
<212> TYPE: DNA

-continued

```
<213> ORGANISM: Artificial Sequence
<220> FEATURE:
<223> OTHER INFORMATION: IsPETase_mut

<400> SEQUENCE: 1
catatgcaga ccaatccgta tgcgcgtggc ccgaatccga ccgcggcgag cctggaagcg      60
agcgcgggtc cgtttaccgt gcgtagcttt accgtgagcc gtccgagcgg ttatggtgcg     120
ggtaccgttt actatccgac caacgcgggt ggcaccgtgg gtgcgatcgc gattgttccg     180
ggttataccg cgcgtcagag cagcatcaaa tggtggggtc cgcgtctggc gagccacggt     240
ttcgtggtta tcaccattga caccaacagc accctggatc agccggaaag ccgtagcagc     300
cagcaaatgg cggcgctgcg tcaagttgcg agcctgaacg gtaccagcag cagcccgatc     360
tacggcaagg tggacaccgc gcgtatgggc gttatgggtt ggagcatggg tggcggtggc     420
agcctgatta gcgcggcgaa caacccgagc ctgaaagcgg cggcgccgca agcgccgtgg     480
catagcagca ccaacttcag cagcgtgacc gttccgaccc tgatctttgc gtgcgagaac     540
gacagcattg cgccggtgaa cagcagcgcg ctgccgatct acgatagcat gagccgtaac     600
gcgaagcagt ccctggaaat taacggtggc agccacagct gcgcgaacag cggtaacagc     660
aaccaagcgc tgattggcaa gaaaggtgtt gcgtggatga acgttttat ggacaacgat      720 acccgttata gcacctttgc gtgcgaaaat ccgaatagca ccgcggtgag cgacttccgt     780
accgcgaact gcagctaact cgag                                              804

<210> SEQ ID NO 2
<211> LENGTH: 1767
<212> TYPE: DNA
<213> ORGANISM: Artificial Sequence
<220> FEATURE:
<223> OTHER INFORMATION: IsMHETase_mut

<400> SEQUENCE: 2
catatgggtg gtggtagcac cccgctgccg ctgccgcaac aacaaccgcc gcaacaggag       60
ccgccgccgc cgccggttcc gctggcgagc cgcgcggcgt gcgaggcgct gaaggatggc      120
aacggtgaca tggtgtggcc gaacgcggcg accgtggttg aagttgcggc gtggcgtgat      180
gcggcgccgg cgaccgcgag cgcggcggcg ctgccggagc actgcgaagt gagcggtgcg      240
atcgcgaagc gtaccggcat tgacggttac ccgtatgaga tcaaatttcg tctgcgtatg      300
ccggcggagt ggaacggccg tttctttatg gaaggtggca gcggtaccaa cggtagcctg      360
agcgcggcga ccggtagcat cggtggcggt cagattgcga gcgcgctgag ccgtaactt      420 gcgaccattg cgaccgatgg cggtcacgac aacgcggtga cgataaccc ggatgcgctg       480 ggtaccgttg cgttcggtct ggacccgcaa gcgcgtctgg acatgggcta caacagctat     540
gatcaggtta cccaagcggg caaggcggcg gttgcgcgtt ctacggtcg tgcggcggac       600 aaaagctatt ttatcggctg cagcgagggc ggtcgtgagg gtatgatgct gagccagcgt     660
ttcccgagcc attatgatgg tattgtggcg ggtgcgccgg gttatcaact gccgaaggcg     720
ggcattagcg gtgcgtggac cacccaaagc ctggcgccgg cggcggtggg cctggacgcg     780
caaggtgttc cgctgattaa caaaagtttt agcgacgcgg atctgcacct gctgagccag     840
gcgatcctgg gtacctgcga tgcgctggac ggcctggcgg atggtattgt tgacaactat     900
cgtgcgtgcc aagcggcgtt tgatccggcg accgcggcga accggcgaa cggtcaggcg       960 ctgcaatgcg ttggtgcgaa aaccgcggac tgcctgagcc cggtgcaggt taccgcgatc    1020
aaacgtgcga tggcgggtcc ggttaacagc gcgggtaccc cgctgtacaa ccgttgggcg    1080
```

-continued

```
tgggatgcgg gtatgagcgg tctgagcggt accacctata accagggctg gcgttccgcg    1140
tggctgggta gcttcaacag cagcgcgaac aacgcgcaac gtgtgagcgg tttcagcgcg    1200
cgtagctggc tggttgactt cgcgaccccg ccggaaccga tgccgatgac ccaggttgcg    1260
gcgcgtatga tgaagttcga ctttgatatc gacccgctga aaatttgggc gaccagcggc    1320
cagttcaccc aaagcagcat ggattggcat ggtgcgacca gcaccgatct ggcggcgttt    1380
cgtgaccgtg gcggtaaaat gatcctgtat catggtatga gcgatgcggc gttcagcgcg    1440
ctggataccg cggactacta tgaacgtctg ggtgcggcga tgccgggtgc ggcgggtttc    1500
gcgcgtctgt ttctggttcc gggtatgaac cattgcagcg gcggtccggg taccgatcgt    1560
tttgacatgc tgaccccgct ggttgcgtgg gttgagcgtg gtgaagcgcc ggatcaaatc    1620
agcgcgtgga gcggtacccc gggttacttc ggtgtggcgg cgcgtacccg tccgctgtgc    1680
ccgtatccgc aaattgcgcg ttacaagggc agcggtgaca tcaataccga agcgaacttt    1740
gcgtgcgcgg cgccgccgta actcgag                                        1767
```

<210> SEQ ID NO 3
<211> LENGTH: 801
<212> TYPE: DNA
<213> ORGANISM: Artificial Sequence
<220> FEATURE:
<223> OTHER INFORMATION: IsMHETase_wt

<400> SEQUENCE: 3

```
catatgcaaa caaacccta tgctcggggc cccaaccta cagccgcttc attggaagct      60
agcgccggtc cgtttaccgt acgctcattt acggtgagcc ggcctagtgg ttatggtgcg     120
gggaccgtgt attaccctac aaatgccggc ggtactgtgg gcgcaattgc gatcgtgccg     180
ggctataccg cgcgtcagtc gtctattaaa tggtggggcc cacgtttagc atcacacgga     240
tttgtagtca ttactattga caccaacagt acgcttgatc agccgtcatc tcgatccagt     300
cagcagatgg ccgcgctgag acaagttgcg tctctcaatg gcacgagcag ctcaccgata     360
tacggtaaag ttgatactgc acgtatgggg gttatgggat ggtccatggg cggtggcggc     420
tctctaatca gtgccgcgaa taatccgtcg ctgaaagctg cagcaccgca ggccccatgg     480
gatagttcga ctaacttctc atcggtcacc gtaccaacgc tgatatttgc ttgcgaaaat     540
gacagtattg ccccggtcaa ttcgtccgct ttaccgatct atgatagcat gtcacgcaat     600
gcgaagcaat ttttggagat taatggtgga tcccattctt gtgctaatag cggaaatagc     660
aatcaagcgc ttatcggcaa gaaaggcgtt gcatggatga aacgcttcat ggataatgat     720
acgaggtact ccacattcgc ctgtgaaaat ccaaacagca cacgagtttc tgactttcgt     780
accgccaatt gcagtctcga g                                              801
```

<210> SEQ ID NO 4
<211> LENGTH: 1767
<212> TYPE: DNA
<213> ORGANISM: Artificial Sequence
<220> FEATURE:
<223> OTHER INFORMATION: IsMHETase_wt

<400> SEQUENCE: 4

```
catatgggtg gtggtagcac cccgctgccg ctgccgcaac aacaaccgcc gcaacaggag      60
ccgccgccgc cgccggttcc gctggcgagc cgcgcggcgt gcgaggcgct gaaggatggc     120
aacggtgaca tggtgtggcc gaacgcgcg accgtggttg aagttgcggc gtggcgtgat     180
```

-continued

```
gcggcgccgg cgaccgcgag cgcggcggcg ctgccggagc actgcgaagt gagcggtgcg    240
atcgcgaagc gtaccggcat tgacggttac ccgtatgaga tcaaatttcg tctgcgtatg    300
ccggcggagt ggaacggccg tttctttatg gaaggtggca gcggtaccaa cggtagcctg    360
agcgcggcga ccggtagcat cggtggcggt cagattgcga gcgcgctgag ccgtaacttt    420
gcgaccattg cgaccgatgg cggtcacgac aacgcggtga acgataaccc ggatgcgctg    480
ggtaccgttg cgttcggtct ggacccgcaa gcgcgtctgg acatgggcta caacagctat    540
gatcaggtta cccaagcggg caaggcggcg gttgcgcgtt tctacggtcg tgcggcggac    600
aaaagctatt ttatcggctg cagcgagggc ggtcgtgagg gtatgatgct gagccagcgt    660
ttcccgagcc attatgatgg tattgtggcg ggtgcgccgg gttatcaact gccgaaggcg    720
ggcattagcg gtgcgtggac cacccaaagc ctggcgccgg cggcggtggg cctggacgcg    780
caaggtgttc cgctgattaa caaaagtttt agcgacgcg atctgcacct gctgagccag     840
gcgatcctgg gtacctgcga tgcgctggac ggcctggcgg atggtattgt tgacaactat    900
cgtgcgtgcc aagcggcgtt tgatccggcg accgcggcga acccggcgaa cggtcaggcg    960
ctgcaatgcg ttggtgcgaa aaccgcggac tgcctgagcc cggtgcaggt taccgcgatc   1020
aaacgtgcga tggcgggtcc ggttaacagc gcgggtaccc cgctgtacaa ccgttgggcg   1080
tgggatgcgg gtatgagcgg tctgagcggt accacctata accagggctg gcgttcctgg   1140
tggctgggta gcttcaacag cagcgcgaac aacgcgcaac gtgtgagcgg tttcagcgcg   1200
cgtagctggc tggttgactt cgcgaccccg ccggaaccga tgccgatgac ccaggttgcg   1260
gcgcgtatga tgaagttcga ctttgatatc gacccgctga aaatttgggc gaccagcggc   1320
cagttcaccc aaagcagcat ggattggcat ggtgcgacca gcaccgatct ggcggcgttt   1380
cgtgaccgtg gcggtaaaat gatcctgtat catggtatga gcgatgcggc gttcagcgcg   1440
ctggataccg cggactacta tgaacgtctg ggtgcggcga tgccgggtgc ggcgggtttc   1500
gcgcgtctgt ttctggttcc gggtatgaac cattgcagcg gcggtccggg taccgatcgt   1560
tttgacatgc tgaccccgct ggttgcgtgg gttgagcgtg gtgaagcgcc ggatcaaatc   1620
agcgcgtgga gcggtacccc gggttacttc ggtgtggcgg cgcgtacccg tccgctgtgc   1680
ccgtatccgc aaattgcgcg ttacaagggc agcggtgaca tcaataccga agcgaacttt   1740
gcgtgcgcgg cgccgccgta actcgag                                       1767
```

CHEMICAL AND BIOLOGICAL INTEGRATED DEGRADATION PROCESS FOR POLYETHYLENE TEREPHTHALATE (PET), FOR RECYCLING PET

CROSS REFERENCE TO RELATED APPLICATIONS

This application is a National Stage of International Application No. PCT/KR2022/002784 filed Feb. 25, 2022, claiming priority based on Korean Patent Application No. 10-2021-0026729 filed Feb. 26, 2021, the entire disclosures of which are incorporated herein by reference.

INCORPORATION BY REFERENCE OF SEQUENCE LISTING

The content of the electronically submitted sequence listing, file name: Q287452_sequence listing as filed.TXT; size: 7,713 bytes; and date of creation: Aug. 23, 2023, filed herewith, is incorporated herein by reference in its entirety.

TECHNICAL FIELD

The present invention relates to a chemical and biological integrated depolymerization process for polyethylene terephthalate (PET) for recycling PET.

BACKGROUND ART

The main units constituting polyethylene terephthalate (PET) are a polyester of terephthalic acid (TPA) and ethylene glycol (EG), which are crosslinked by ester bonds. There are three known main methods for recycling PET. The first method is an energy recovery method through incineration and pyrolysis, and this method is generally used but has disadvantages of undesirable by-products, carbon dioxide and chemicals, and low efficiency. The second method is physical recycling for producing secondary plastic through crushing and remelting, and has a disadvantage of decreased quality. The above two methods are low utilization methods, and the value of the results thereby is low. The third method is chemical recycling, which depends on a solvent. When water is used, it is hydrolysis, when an amine is used, it is aminolysis, when an alcohol is used, it is alcoholysis, and when a glycol is used, it is glycolysis. However, this method also requires harsh conditions, so it is difficult to be applied on an industrial scale. In addition, since the original purpose of chemical recycling is to obtain high-purity monomers and thus make virgin plastic again, separation and purification processes for obtaining monomers are needed. This method has a disadvantage of being economically less efficient than a conventional plastic production process.

Biological recycling of PET is still at an early stage. This method has the advantage in that PET upcycling is possible because PET can be converted into high-value products through bioconversion. However, it is difficult to hydrolyze PET using only an enzyme, making practical application difficult. Therefore, to facilitate enzymatic hydrolysis, it is necessary to create a substrate preferred by an enzyme by introducing a chemical pretreatment process for PET. Accordingly, it is important to find a chemical pretreatment process suitable for a biological process. In addition, a proper strain has to be used to convert an enzymatic hydrolysate into a high-value platform chemical.

RELATED ART DOCUMENT

Patent Document

Korean Unexamined Patent Application No. 10-2020-0119213

DISCLOSURE

Technical Problem

The present invention is directed to providing an effective chemical-biological integrated process, which is able to produce high-value products using components of polyethylene terephthalate (PET) as resources to effectively upcycle PET.

There are three things required to build the integrated process. First, a substrate preferred by an enzyme has to be produced by introducing a chemical pretreatment process for PET, and second, substrates to be used in bioconversion, that is, terephthalic acid and ethylene glycol, have to be effectively produced using an enzyme. Third, the produced terephthalic acid and ethylene glycol have to be well converted into high-value products, protocatechuic acid (PCA) and glycolic acid (GLA), respectively.

First, as a first chemical pretreatment process for PET, glycolysis using glycol is used, and glycolysis conventionally uses an ethylene glycol solvent and a metal catalyst. However, the use of a metal catalyst may have an adverse effect on not only the environment but also a subsequent biological process. Second, PET decomposed into an oligomer by the glycolysis is decomposed into terephthalic acid and ethylene glycol using a hydrolase. The terephthalic acid produced at this time is a dicarboxylic acid that lowers the pH of an enzymatic hydrolysis condition, and as a result, enzymatic activity is suppressed, which is an obstacle to producing a high concentration product.

Accordingly, to solve the above problem, in the present invention, the chemical pretreatment process that decomposes PET into an oligomer uses ethylene glycol (EG) as a solvent, betaine as an eco-friendly catalyst, and then, by selecting an appropriate buffer concentration and pH in the enzymatic hydrolysis, a reduction in pH of the enzymatic hydrolysis conditions due to the influence of TPA is prevented. In addition, recombinant *E. coli* into which a recombinant plasmid having a conversion-related gene for converting TPA into PCA is inserted was used, and *Gluconobacter oxydans* (*G. oxydans*) KCCM 40109 with a conversion pathway to convert EG into GLA was used. By this conversion method using bacteria such as whole-cell conversion, a high-concentration and high-yield product was rapidly obtained. In addition, substrates in all processes use the products of previous processes as they are, so there is no additional purification process.

Technical Solution

To solve the above problems, the present inventors used a chemical pretreatment process that decomposes PET into an oligomer, and this process uses ethylene glycol (EG) as a solvent, betaine as an eco-friendly catalyst, and hydrolyzes the PET oligomer into TPA and EG using PET hydrolase (IsPETase) and mono(2-hydroxyethyl) terephthalate (MHET) hydrolase (IsMHETase). Afterward, recombinant *E. coli* into which a recombinant plasmid having a conversion-related gene for converting TPA into PCA is inserted was used, and *G. oxydans* KCCM 40109 having a conversion pathway to convert EG to GLA was used. This is a conversion method using bacteria, and a high-concentration and high-yield product was rapidly obtained using whole-cell conversion. In addition, substrates in all processes use the products of previous processes as they are, so there is no additional purification process.

PET is a polymer in which hundreds to tens of thousands of 'monomers,' which are small molecular units, are inter-twined like chains. Since it is difficult to decompose PET naturally, PET is incinerated or buried, causing various environmental problems. Methods of depolymerizing PET into monomers using enzymes such as PETase have been developed, but these enzymes have a long depolymerization time and cause a small amount of depolymerization. When PET is decomposed into an oligomer using ethylene glycol before depolymerizing PET with an enzyme, the same amount of PET may be decomposed into a larger amount of monomers. In addition, it was confirmed that, when PET is glycolyzed into an oligomer using ethylene glycol, 'betaine' may be used as a catalyst. Betaine is a 'zwitterion' with both a cation and an anion and is made when an animal, a plant, and a microorganism are exposed to environmental stresses such as osmotic pressure, high temperature, and dehydra-tion. It was confirmed that betaine enables ethylene glycol to easily break bonding chains of PET, helping oligomer sepa-ration.

In addition, in terms of effectiveness, as a result of comparing amounts of monomers produced when undergo-ing or nor undergoing the process of forming PET into an oligomer using ethylene glycol and betaine, it was con-firmed that the amount of monomer produced by the process of converting PET into an oligomer is larger than that of monomers produced when PET is decomposed using an enzyme from the beginning. Moreover, betaine has the advantage of not using the process of separating intermedi-ate by-products every time because it does not affect the enzyme used when an oligomer is formed into a monomer.

Therefore, the present invention provides a method for depolymerizing PET into an oligomer using glycolysis as process, with betaine acting as a catalyst.

In addition, the present invention provides a method of producing a high-value compound from PET, which includes:

producing bis(2-hydroxyethyl) terephthalate (BHET) through the glycolysis of PET in the presence of betaine as a catalyst;

depolymerizing the produced BHET into terephthalic acid and ethylene glycol via a mono(2-hydroxyethyl) tere-phthalate (MHET) intermediate through enzymatic hydrolysis; and converting the terephthalic acid into protocatechuic acid through bioconversion in the presence of a biocatalyst, or converting the ethylene glycol into glycolic acid through fermentation (FIG. 1).

In this method, the glycolysis of depolymerizing PET into an oligomer may be performed by applying microwaves in an ethylene glycol solvent using betaine as a catalyst. Specifically, the glycolysis may be performed in a molar ratio (PET:EG) of 1:3 to 20 using 0.1 to 1 wt % (catalyst/PET, w/w ratio) of betaine, relative to a PET substrate, at 190° C. for 10 minutes to 2 hours. In specific embodiments, when glycolysis was performed in a molar ratio (PET:EG) of 1:4 using 0.5 wt % (catalyst/PET, w/w ratio) of betaine, relative to a PET substrate, at 190° C. for 1 hour, the yield of BHET was highest.

BHET produced by PET glycolysis was hydrolyzed into MHET by PETase (IsPETase), and the MHET may be hydrolyzed into terephthalic acid and ethylene glycol by mono(2-hydroxyethyl) terephthalate (MHET) hydrolase (IsMHETase).

IsPETase and IsMHETase, which hydrolyze the oligom-ers of PET, BHET and MHET, respectively, may be wild-type or mutant-type. The wild-type IsPETase and IsMHETase may consist of the base sequences represented by SEQ ID NO: 3 and SEQ ID NO: 4, respectively. In exemplary embodiments of the present invention, as the enzymes, mutant-type IsPETase and IsMHETase were used, wherein the mutant-type IsPETase (IsPETase$^{Mut}$) may con-sist of the base sequence represented by SEQ ID NO: 1, and the mutant-type IsMHETase (IsMHETase$^{Mut}$) may consist of the base sequence represented by SEQ ID NO: 2.

The bioconversion of terephthalic acid into protocat-echuic acid may be performed using a microorganism expressing terephthalic acid 1,2-dioxygenase and 1,2-dihy-droxy-3,5-cyclohexadiene-1,4-dicarboxylate (DCD) dehy-drogenase as a biocatalyst. The terephthalic acid (TPA) 1,2-dioxygenase converts TPA into DCD, and the DCD dehydrogenase converts DCD into PCA. The TPA 1,2-dioxygenase and the DCD dehydrogenase may be derived from *Comamonas* sp. E6, and the names of coding genes are TphAabc and TphB, respectively. The enzymes may use NADH and NADPH as cofactors. According to one embodi-ment of the present invention, to obtain PCA from the PET hydrolysate TPA, microorganisms expressing TphAabc and TphB may be used as biocatalysts.

The term "biocatalyst" used herein refers to an enzyme involved in bioconversion of terephthalic acid, and is used in combination with a microorganism expressing the enzyme. The enzyme may be expressed by being introduced into host cells in the form of a recombinant vector including a coding gene.

The fermentation of ethylene glycol may be performed using ethylene glycol-fermenting microorganisms, which include one or more selected from the group consisting of *G. oxydans* KCCM 40109, *Clostridium glycolicum*, and *Pseudomonas putida*.

Afterward, the final product protocatechuic acid may be converted into one or more high-value compounds selected from the group consisting of gallic acid, pyrogallol, cat-echol, muconic acid and vanillic acid through bioconver-sion. A detailed bioconversion method relating thereto is disclosed in Korean Unexamined Patent Application No. 10-2020-0119213A.

Advantageous Effects

According to the technology of the present invention, a novel, efficient and economical chemical-biological inte-grated process for PET upcycling is suggested. Here, using the process of the present invention, there is no need for additional separation and purification processes between chemical and biological processes, and finally, platform chemicals, PCA and GLA, can be produced from PET at high concentrations with high yields.

DESCRIPTION OF DRAWINGS

FIG. 1 is an overall schematic diagram of a chemical-biological integrated process for producing platform chemi-cals used in PET upcycling.

FIGS. 2*a* to 2*h* show the result of confirming the product of PET glycolysis using betaine as a catalyst. FIG. 2*a* is the schematic diagram of PET glycolysis using betaine. FIG. 2*b* is the result of measuring the PET glycolysis product obtained using betaine as a catalyst through Fourier transform infrared spectroscopy (FT-IR). As a control, a PET glycolysis mixture was measured before the reaction, and a purified material obtained from the PET glycolysis product and a BHET standard were measured after the reaction. FIG. 2*c* is the result of measuring an oligomer obtained from the PET glycolysis mixture through FT-IR after the reaction. As a control, before the reaction, PET plastic granules were used. FIG. 2*d* is a total ion chromatogram (TIC) result for the PET glycolysis product and the BHET standard using a gas chromatography-mass spectrum (GC/MS). FIG. 2*e* is the mass spectrum of the PET glycolysis product. FIG. 2*f* is the mass spectrum of the BHET standard. FIG. 2*g* is the 1D $^1$H spectrum result measured from the purification material obtained from the PET glycolysis mixture and the BHET standard through nuclear magnetic resonance spectroscopy (NMR) after the reaction. FIG. 2*h* is the 1D $^{13}$C spectrum result measured from the purification material obtained from the PET glycolysis mixture and the BHET standard through nuclear magnetic resonance spectroscopy (NMR) after the reaction.

FIG. 3 shows the predicted structure of the interaction between the PET polymer and EG, and betaine, and the result of comparing interaction energy levels through density functional theory (DFT) analysis.

FIG. 4 is the predicted mechanism of PET glycolysis using betaine as a catalyst. (A) is the most stable interactive structure between the PET polymer and EG, and betaine, confirmed through the DFT analysis. (B) is the schematic diagram for the predicted mechanism of PET glycolysis when betaine acts as a catalyst based on the structure.

FIG. 5 shows the comparison in enzymatic activity between a wild-type enzyme and a mutant enzyme. (A) is the result of comparing enzyme activity by temperature between the wild-type PETase (IsPETase$^{Wild}$) and the mutant PETase (IsPETase$^{Mut}$) for PET granules. (B) is the result of comparing enzymatic activity by temperature between the wild-type mono(2-hydroxyethyl) terephthalate (MHET) hydrolase (IsMHETase$^{Wild}$) and the mutant mono (2-hydroxyethyl) terephthalate (MHET) hydrolase (IsMHETase$^{Mut}$) for mono(2-hydroxyethyl) terephthalate (MHET).

FIGS. 6*a* to 6*m* show the result of the optimization of conditions for enzymatic hydrolysis using a PET glycolysis product as a substrate. FIG. 6*a* is the result of comparing the inhibitory effects of various heavy metal ions including betaine on IsPETase$^{Mut}$ and IsMHETase$^{Mut}$. FIG. 6*b* is the result of measuring the initial rates of IsPETase$^{Mut}$ and IsMHETase$^{Mut}$ according to the amount of an enzyme relative to a substrate. FIG. 6*c* is the result of measuring TPA, which is a product obtained with different inoculation amounts of IsPETase$^{Mut}$ and IsMHETase$^{Mut}$ using 50 mM sodium phosphate buffer (pH 8) and the PET glycolysis product as a substrate under enzymatic hydrolysis conditions. FIG. 6*d* is the result of confirming the buffering capacity of 50 mM sodium phosphate buffer by visually displaying the pH value using pH paper when different TPA concentrations were added in 50 mM sodium phosphate buffer (pH 8). FIG. 6*e* is the result of measuring the relative activity of IsPETase$^{Mut}$ by pH. FIG. 6*f* is the result of confirming a pH change using pH paper when the enzyme inoculation amount is 9.0 U/L among the results of (C). FIG. 6*g* is the result of measuring TPA, which is a product obtained when bicine-NaOH buffer (pH 8) was added at 50 mM to 1 M under enzymatic hydrolysis conditions and each of the inoculation amounts of IsPETase$^{Mut}$ and IsMHETase$^{Mut}$ is 2.3 U/L, over time. FIG. 6*h* is the HPLC analysis result for the products before and after reaction when 1 M bicine-NaOH buffer (pH 8) is used under enzymatic hydrolysis conditions, and BHET is used as a substrate. As standards, BHET, MHET and TPA were used. FIG. 6*i* is the HPLC analysis result for the products before and after a reaction when 1 M Tris-HCl buffer (pH 8) is used under enzymatic hydrolysis conditions, and BHET is used as a substrate. As standards, BHET, MHET and TPA are used. FIG. 6*j* is the result of measuring TPA, which is a product obtained when 1 M bicine-NaOH buffer (pH 8) is used under enzymatic hydrolysis conditions, a PET glycolysis product is used as a substrate, and different amounts of IsPETase$^{Mut}$ and IsMHETase$^{Mut}$ are inoculated, over time. FIG. 6*k* is the result of measuring TPA, which is a product obtained when 1 M bicine-NaOH buffer (pH 8) is used under enzymatic hydrolysis conditions, different concentrations of a PET glycolysis product are used as a substrate, and a corresponding enzyme inoculation amount is 2.3 U/L, over time. FIG. 6*l* shows the yields of the PET and BHET substrates added at 12 hours among the FIG. 6*k* result. FIG. 6*m* is the comparison of enzymatic activities using PET granules, an oligomer obtained from PET glycolysis, a PET glycolysis product, and BHET as substrates.

FIG. 7 is the result of whole-cell conversion using an enzymatic hydrolysate as a substrate. (A) is the schematic diagram of the pathway of biosynthesis of TPA into PCA. (B) is the result of measuring a product PCA and a substrate TPA, which are obtained when whole-cell conversion is performed using a TPA standard and an enzymatic hydrolysate as substrates, and recombinant *E. coli* as a strain, over time. (C) is the yield of produced PCA relative to consumed TPA. (D) is the schematic diagram of the pathway of biosynthesis of EG into GLA. (E) is the result of measuring a product GLA and a substrate EG over time, when whole-cell conversion is performed using an EG standard and an enzyme hydrolysate as substrates, and *G. oxydans* is used as a strain. (F) is the yield of produced GLA relative to consumed EG.

MODES OF THE INVENTION

Hereinafter, the present invention will be described in further detail with reference to examples, but the scope of the present invention is not limited by the examples suggested below.

<Example 1> PET Glycolysis Using Betaine as Catalyst

To establish an economical and efficient PET upcycling process, a chemical PET depolymerization process is required. However, considering a chemical-biological integrated process for eco-friendly and sustainable PET upcycling, it is important to ensure that the results of a chemical process do not adversely affect a subsequent biological process. A conventional PET glycolysis method mainly used a heavy metal catalyst. The use of a metal catalyst may have an adverse effect on the biological process of the integrated process and have adverse environmental effects, so glycolysis was performed in a microwave digestion system using betaine instead of a metal catalyst. Specifically, 3.5 to 11.5 g of granular PET and a specific amount of EG were reacted using betaine as a catalyst at 190° C. for 30 to 120 minutes. To maintain the reaction conditions, a microwave digester (Milestone, Shelton, CT) with a thermocouple and magnetic stirrer function was used, and the reaction was performed in a 100 mL reaction vessel for exclusive use of a microwave digester.

To determine the glycolysis effect of betaine, first, the input amount of a substrate was optimized. Glycolysis was performed at 190° C. for 30 minutes by adding 0.5% (catalyst/PET, w/w ratio) betaine to a PET substrate and an EG solvent at a molar ratio (PET:EG) of 1:3, 1:4, 1:5, 1:6, 1:10, or 1:20. Here, the major product BHET and a by-product MHET were produced. The BHET and MHET concentrations were measured by liquid chromatography. As a result, it was confirmed that the highest yield was obtained under a substrate input condition corresponding to a PET:EG molar ratio of 1:5. However, considering the concentration of the final product, it was confirmed that the yield was even higher under the substrate input condition corresponding to the PET:EG molar ratio of 1:4. This result is based on that, considering process efficiency and economic feasibility, the substrate input condition corresponding to a PET:EG molar ratio of 1:4, which can obtain a high concentration product, is optimal. Accordingly, the substrate input condition corresponding to a PET:EG molar ratio of 1:4 was selected, and further conditions were established (Table 2).

To confirm the catalytic effect on the input amount of betaine, betaine corresponding to 0, 0.1, 0.5, 1% (catalyst/PET, w/w ratio) was added, and glycolysis was performed at 190° C. for 30 minutes. As a result, it was confirmed that the condition of adding betaine corresponding to 0.5% (catalyst/PET, w/w ratio) is optimal. Accordingly, this condition was selected, and further conditions were established (Table 2).

Next, to confirm the effect by glycolysis reaction time, the reaction was performed at 190° C. under various reaction time conditions of 30, 60, 90, and 120 minutes. As a result, it was confirmed that 60 minutes is the optimal condition. Finally, under glycolysis conditions including a substrate input corresponding to a PET:EG molar ratio of 1:4, betaine added at 0.5% (catalyst/PET, w/w ratio), and heating at 190° C. for 60 minutes, a yield of 58.7%, and concentrations of 368.6 g/L of BHET and 32.8 g/L of MHET were obtained. Afterward, in a biological process, the PET glycolysis product that had been produced under the above conditions was used as a substrate (Table 2).

Additionally, compared to the case of using 1,5,7-triaz-abicyclo[4.4.0]dec-5-ene (TBD), which is a known representative organic catalyst used for glycolysis of conventional PET, as a result of using betaine and TBD as catalysts under the same conditions, it was confirmed that BHET can be obtained in a higher yield than the case of using betaine (Table 2).

To analyze a PET glycolysis product using betaine as a catalyst, high performance liquid chromatography (HPLC) analysis was performed. HPLC analysis conditions are as follows. As a column, a C18 column (OpitmaPak C18-51001546, 5 μm, 150 mm×4.6 mm) was used, and a column temperature was maintained at 25° C. during the analysis. Two mobile phases, A and B, were used, wherein A is 0.1% trifluoroacetic acid in distilled water, and B is methanol. During the analysis at a flow rate of 1 mL/min for 27 minutes, the proportion of the mobile phase B was maintained at 5% at 0 to 2 minutes, and the proportion of the mobile phase B was changed from 5 to 57% at 2 to 18 minutes. At 18 to 22 minutes, the proportion of the mobile phase B was changed from 57 to 5%. Finally, at 22 to 27 minutes, the proportion of the mobile phase B was maintained at 5%. Chromatography was performed at a wavelength of 254 nm using a UV/Vis detector.

As a result, FIG. 2a is the schematic view of PET glycolysis using betaine as a catalyst, visualizing changes before and after actual analysis. Referring to FIG. 2b, a mixture before PET glycolysis, a PET glycolysis product, a water-soluble material obtained from the PET glycolysis product, and a BHET standard were subjected to Fourier transform infrared spectroscopy (FT-IR). Due to the hydroxyl group of EG used as a solvent in the mixture before PET glycolysis, a broad peak may be identified between the wavenumbers 3050 to 3600 cm$^{-1}$. For the PET glycolysis product, a new hydroxyl group peak may be identified at the wavenumber 3436 cm$^{-1}$. This is caused by a hydroxyl group newly formed by PET glycolysis. For a purified material obtained from the PET glycolysis product and the BHET standard, a sharp peak was identified at the wavenumber 3436 cm$^{-1}$. Comparing the analysis result of each sample, it can be seen that, because a sharp peak is shown at the wavenumber 3436 cm$^{-1}$ for the PET glycolysis product, BHET is produced through PET glycolysis using betaine. In FIG. 2c, a precipitate (oligomer) obtained by washing the PET granules and the PET glycolysis product with distilled water was subjected to FT-IR. A broad peak can be seen around the wavenumber 3387 cm$^{-1}$ for the precipitate sample. This indicates a hydroxyl group, and in the case of the PET granule sample, since the proportion of terminals is low relative to a molecular length, a hydroxyl group peak cannot be identified. Therefore, it can be seen that PET is decomposed by PET glycolysis using betaine. In order to confirm whether the main product of PET glycolysis is BHET, the PET glycolysis product and the BHET standard were measured using GC/MS. First, for GC/MS, a derivatization process is as follows. The PET glycolysis product and the BHET standard dissolved in methanol were centrifuged for 10 minutes. Subsequently, 20 μL of the supernatant was dehydrated using Speed Vac. For derivatization, 10 μL of 4% (w/v) O-methylhydroxylamine hydrochloride in pyridine was added to the dehydrated sample and reacted at 30° C. for 90 minutes. Afterward, 45 μL of N-methyl-N-(trimethylsilyl)trifluoroacetamide was added and further reacted at 37° C. for 30 minutes. Here, for analysis, RTX-5Sil MS (30 m×0.25 mm i.d., 25 μm film thickness, Resteck) column-attached Agilent 7890A GC/5975C MSD system was used. The column temperature was first maintained at 150° C. for 1 minute, raised to 330° C. at 20° C./min, and then maintained for 5 minutes. 1 μL of the sample was analyzed using a splitless method. According to the total ion chromatography (TIC) result of FIG. 2d, it was confirmed that the peak of the PET glycolysis product corresponds to the BHET peak. FIGS. 2e and 2f show the mass spectra of the PET glycolysis product and the BHET standard, respectively. In addition, the PET glycolysis product and the BHET standard were subjected to nuclear magnetic resonance (NMR). Both samples were dissolved in dimethyl sulfoxide. The analysis was carried out by experimentation and measurement at 298 K and 900 MHz using a Bruker Avance II spectrometer. As a result, from the 1D $^1$H spectrum of FIG. 2g and the 1D $^{13}$C spectrum of FIG. 2h, it was confirmed that the PET glycolysis product and the BHET standard are the same.

<Example 2> Density Functional Analysis for PET Glycolysis Using Betaine as Catalyst and Catalytic Mechanism of Betaine Under the circumstances of PET glycolysis, in which betaine, EG, and the PET polymer are mixed, the present inventors tried to understand how these three materials interact, and thereby identify the catalytic mechanism of betaine. In FIG. 3, six models that can predict where betaine, EG, and the PET polymer are located are proposed, and it was confirmed what is the most stable interaction between models through DFT analysis. After deducing gas phase energy of the predicted models using Jaguar (Gaussian) software, the F model of FIG. 3, which is the most stable model, was selected. It was confirmed that the other five models have higher relative energy than the F model. Accordingly, it can be seen that the F model of FIG. 3 is most preferred, and the positions between betaine, EG, and the PET polymer can be known.

Afterward, referring to A of FIG. 4, the interaction bonds and distances between betaine-EG, EG-PET polymer, and PET polymer-betaine of the F model of FIG. 3 were determined. In the interaction structures of the F model, the PET polymer, betaine and EG are tightly connected by hydrogen bonds, compared to other interaction structures. The PET depolymerization mechanism by betaine is shown in B of FIG. 4. The cationic moiety of betaine interacts with the carbonyl oxygen of an ester group of the PET polymer. Therefore, the carbon in the ester group of the PET polymer becomes cationic. Then, oxygen in the hydroxyl group of EG attacks the cationic carbon in the ester group of the PET polymer. Therefore, the betaine, EG, and the PET polymer form a tetrahedral intermediate. Here, the carboxyl group of the betaine attracts hydrogen in a hydroxyl group of EG attacking the cationic carbon in the ester group of the PET polymer. Accordingly, hydrogen in the hydroxyl group of EG is more easily detached. The hydrogen in the hydroxyl group of EG is detached, the bond between the cationic moiety of the betaine and the carbonyl oxygen in the ester group of the PET polymer is broken, and a carbonyl group is formed again. Next, the acyl-oxygen bond is broken, breaking off one chain of the PET polymer. Finally, one side of the ester group of the PET polymer is replaced with EG used as a solvent. This reaction proceeds countlessly, producing the final product, BHET.

<Example 3> Preparation of Enzyme Capable of Depolymerizing PET Glycolysis Product Enzymes that decompose PET may be confirmed as in Table 1. Before IsPETase and IsMHETase derived from *Ideonella sakaiensis*, which can decompose PET, were found in 2016, lipase and cutinase had been known as the enzymes that decompose PET. Since these enzymes do not specifically decompose PET, their activities were low. However, IsPETase and IsMHETase have the activity of specifically depolymerizing PET. However, their wild-types merely have higher activity than previously known enzymes, but still have lower activity when compared to other recycling methods, and thus they were difficult to be applied to the process. Recently, the structures of the IsPETase and the IsMHETase have been identified, and mutant-type IsPETase and IsMHETase for increasing activity have been studied. Therefore, in this study, mutant-type IsPETase$^{Mut}$ and IsMHETase$^{Mut}$ (Table 2), not the wild-type enzymes, were used. Each gene sequence was codon-optimized and ligated to NdeI and XhoI sites of a pET28a vector, constructing pET28a_IsPETase$^{Mut}$ and pET28a_IsMHETase$^{Mut}$ plasmids. These plasmids were transformed into *E. coli* DH5α.

To overexpress genes thus obtained, *E. coli* BL21(DE3), which is a host for protein expression, was transformed. BL21(DE3)_pET28a_IsPETase$^{Mut}$ was cultured using a Luria-Bertani (LB) medium containing 40 mg/L kanamycin at 37° C. until 600 nm absorbance reached 0.5. To induce protein expression, 0.5 mM IPTG was added, and an induction temperature was set to 16° C., overexpressing a protein in a water-soluble form for 18 hours. After the culture, the cells were collected by centrifugation, dissociated using 20 mM Tris-HCl buffer (pH 7.4), and disrupted using a sonicator. Through centrifugation at 8,000 g, a supernatant was obtained. The resulting recombinant protein was purified using a HisTrap column (GE Healthcare, Piscataway, USA). For purification, a binding buffer (20 mM sodium phosphate buffer, 500 mM NaCl, 20 mM imidazole, pH 7.4) was flowed through a column. Next, the supernatant obtained by centrifugation was flowed therethrough. Finally, an elution buffer (20 mM sodium phosphate buffer, 500 mM NaCl, 300 mM imidazole, pH 7.4) was flowed therethrough, thereby obtaining purified IsPETase$^{Mut}$ on the elution buffer. The purified protein was concentrated using an Amicon Ultra Centrifugal filter (10,000 MW cutoff; Millipore, Billerica, MA, USA), and the protein concentration was measured using a bicinchoninic acid (BCA) protein assay kit (Thermo Fisher Scientific, San Jose, CA, USA). The expressed IsPETase$^{Mut}$ was determined to be 28.6 kDa through 8% SDS-PAGE.

BL21(DE3)_pET28a_IsMHETase$^{Mut}$ was cultured using an LB medium containing 40 mg/L kanamycin at 37° C. until 600 nm absorbance reached to 0.5. To induce protein expression, 0.5 mM IPTG was added, and an induction temperature was set to 16° C., overexpressing the protein for 16 hours. Here, the recombinant protein was overexpressed as an insoluble protein. After the culture, the cells were collected through centrifugation, dissociated with 8 M urea and 20 mM Tris-HCl buffer (pH 7.4), and disrupted using a sonicator. An aggregated protein was dissolved in a liquid part due to the influence of 8 M urea. Through centrifugation again at 8,000 g, a supernatant was obtained. This recombinant protein was purified using a HisTrap column (GE Healthcare, Piscataway, USA). For purification, a binding buffer (8 M urea, 20 mM Sodium phosphate buffer, 500 mM NaCl, 20 mM imidazole, pH 7.4) was flowed through a column. The supernatant obtained by centrifugation was then flowed therethrough. Finally, an elution buffer (8 M urea, 20 mM sodium phosphate buffer, 500 mM NaCl, 300 mM imidazole, pH 7.4) was flowed therethrough, thereby obtaining the purified IsMHETase$^{Mut}$ on the elution buffer. Through dialysis, 8 M urea of the elution buffer was removed to refold the aggregated IsMHETase$^{Mut}$, thereby obtaining active IsMHETase$^{Mut}$. For the IsMHETase$^{Mut}$, a protein concentration was measured using a bicinchoninic acid (BCA) protein assay kit (Thermo Fisher Scientific, San Jose, CA, USA). The expressed IsMHETase$^{Mut}$ was determined to be 62.8 kDa using 8% SDS-PAGE.

<Example 4> Optimization of High-Concentration TPA and EG Production Through Hydrolase Reaction Using PET Glycolysis Product as Substrate An enzyme experiment was performed to confirm whether the IsPETase$^{Mut}$ and IsMHETase$^{Mut}$ used herein have higher activity and thermal resistance than IsPETase$^{Wild}$ and IsMHETase$^{Wild}$ as reported previously. The experiment for IsPETase was performed in 500 μL of buffer containing 50 mM sodium phosphate (pH 8) using 10 mg of PET granules as a substrate and 500 nM of enzyme, and the experiment for IsMHETase was performed using 5 g/L of MHET as a substrate and 1500 nM of enzyme in 500 μL of buffer containing 50 mM sodium phosphate (pH 8).

The reaction temperatures were 35, 40, 45, and 50° C. After the reaction was performed for 48 hours and 30 minutes, respectively, an enzyme reaction product was diluted in methanol, centrifuged at 25,188 g for 10 minutes, followed by analyzing the supernatant through high performance liquid chromatography (HPLC). As a result, as shown in A and B of FIG. 5, under higher temperature conditions, higher activities were shown. In the temperature conditions, at 40° C., it was confirmed that IsPETase$^{Mut}$ exhibited the highest activity. In addition, at 40° C. and 45° C., it was confirmed that IsMHETase$^{Mut}$ has the highest activity.

To confirm whether the metal catalysts used in conventional PET glycolysis and betaine, which is an eco-friendly catalyst selected in this study, can have inhibitory effects on enzymatic hydrolysis, IsPETase$^{Mut}$ and IsMHETase$^{Mut}$ enzyme experiments were performed using 1 mM each of betaine, Ca$^{2+}$, Co$^{2+}$, Cu$^{2+}$, Fe$^{2+}$, Mg$^{2+}$, Mn$^{2+}$, Ni$^{2+}$, pb$^{2+}$, Zn$^{2+}$, and Li$^+$. The experiments were performed under conditions including an enzyme concentration of 2.3 U/L, 2.5 mg each of the substrates BHET and MHET, 50 mM sodium phosphate buffer (pH 8), and a volume of 500 μL. After performing the reaction at 40° C. for 15 minutes, all samples were diluted in methanol and centrifuged at 25,188 g for 10 minutes, followed by analyzing the supernatant through high performance liquid chromatography (HPLC). As a result, referring to FIG. 6a, unlike the other metal catalysts, it was confirmed that betaine has no inhibitory effect on IsPETase$^{Mut}$ and IsMHETase$^{Mut}$ enzyme reactions. Therefore, the product of PET glycolysis using betaine may be used in enzymatic hydrolysis.

To determine an optimal input amount of the enzyme relative to a substrate under enzymatic hydrolysis reaction conditions, an enzymatic hydrolysis reaction was performed under different enzyme input conditions, and an initial rate was confirmed. The IsPETase$^{Mut}$ and IsMHETase$^{Mut}$ enzyme reaction conditions included 10 g/L of BHET and 5 g/L of MHET as substrates, 50 mM sodium phosphate buffer (pH 8), and a volume of 500 μL. The input amount of IsPETase$^{Mut}$ ranged from 50 to 400 nmol/g BHET, and the input amount of IsMHETase$^{Mut}$ ranged from 300 to 900 nmol/g MHET. After performing the reaction at 40° C. for 10 minutes, all samples were diluted in methanol and centrifuged at 25,188 g for 10 minutes, followed by analyzing the supernatant through high performance liquid chromatography (HPLC). As a result, in FIG. 6b, an initial rate for each enzyme was confirmed. Based on this, 1 unit (U) of IsPETase$^{Mut}$ was defined as the amount of enzyme for producing MHET (100 μmole) from BHET per minute at 40° C. under a condition of pH 8, 1 unit (U) of IsMHETase$^{Mut}$ was defined as an input amount of enzyme producing TPA (100 μmole) from MHET per minute at 40° C. under a condition of pH 8.

Based on the defined enzyme input amounts, a hydrolase reaction was performed using the product of PET glycolysis, in which betaine was used, as a substrate. Accordingly, the efficient input amounts of the IsPETase$^{Mut}$ and IsMHETase$^{Mut}$ enzymes relative to substrates were to be confirmed without wasting the enzymes. The reaction conditions included a PET glycolysis product including 10 g/L of BHET as a substrate, 50 mM sodium phosphate buffer (pH 8), and a volume of 500 μL. After the reaction was performed at 40° C. for 6 hours, 30 min, 1 hr, 3 hr, and 6 hr, samples were diluted in methanol and centrifuged at 25,188 g for 10 minutes, and followed by analyzing the supernatant through high performance liquid chromatography (HPLC). As a result, in FIG. 6c, when the enzyme input amounts are 2.3 U/L and 4.5 U/L, compared to 9.0 U/L, it was confirmed that the amount of the product TPA is low. As the reaction progressed, it was expected that the pH was lowered and the enzyme activity was lost due to the influence of the product TPA. First, to confirm how low the pH is under the enzymatic hydrolysis reaction conditions due to the influence of TPA, TPA was added at a concentration of 0 to 10 g/L under the condition of 50 mM sodium phosphate buffer (pH 8). As a result, in FIG. 6d, the pHs of all samples were measured with a pH meter and visually confirmed with pH paper. The pHs decreased from 8.00 to 5.47 as the TPA concentration was increased from 0 to 4 g/L. Afterward, the pH was maintained at 5.35 to 5.39 until the TPA concentration reached 10 g/L. Accordingly, it was confirmed how low the pH became using TPA produced under the enzymatic hydrolysis reaction conditions.

Next, to check the IsPETase$^{Mut}$ enzyme activity for each pH, the IsPETase$^{Mut}$ enzyme reaction was performed with sodium acetate, sodium phosphate, bicine-NaOH, Tris-HCl, and glycine-NaOH at a concentration of 50 mM at pH 5 to 9. The enzyme reaction conditions included 10 g/L of BHET, 2.3 U/L of the enzyme, and a reaction volume of 500 μL. After the reaction was performed at 40° C. for 1 hour, the samples were diluted in methanol and centrifuged at 25,188 g for 10 minutes, followed by analyzing the supernatant through HPLC. As a result, in FIG. 6e, under the condition of pH 5.5, relative to pH 7.0, it was confirmed that the relative activity decreases to 19.5%. Based on the results of FIGS. 6d and 6e, it was confirmed that, in the enzymatic hydrolysis, as the product TPA increases, the pH of the enzymatic hydrolysis conditions decreases, and the activity of the IsPETase$^{Mut}$ enzyme is drastically reduced due to the influence of low pH.

Again, in FIG. 6c, the pH change over time under the experimental condition of 9.0 U/L was visualized with pH paper and also shown with the standard color per pH of the pH paper in FIG. 6f. At 30 minutes of the reaction, it was confirmed that 5.5 g/L of TPA was produced, and referring to FIGS. 6d and 6e, it can be seen that the activity of the IsPETase$^{Mut}$ enzyme is reduced. Under the experimental conditions of 2.3 U/L and 4.5 U/L, the small amount of the product TPA results from the reduction in enzyme activity. Accordingly, it was confirmed that the pH capacity is an important factor in the enzymatic hydrolysis conditions.

Next, enzymatic hydrolysis was performed under the conditions including 50 to 1,000 mM bicine-NaOH buffer (pH 8), the PET glycolysis product including 10 g/L of BHET as a substrate, and a volume of 500 μL. Each of the input amounts of the IsPETase$^{Mut}$ enzyme and the IsMHETase$^{Mut}$ enzyme was 2.3 U/L. As a result, in FIG. 6g, it can be confirmed that, as the concentration of the bicine-NaOH buffer (pH 8) increases, the product TPA increases over time. As the pH capacity of the enzymatic hydrolysis conditions increases, it can be seen that the pH reduction effect by the product TPA is reduced, maintaining the activity of the enzyme at the pH maintained thereby.

In addition, by confirming that there is no inhibitory effect on enzyme activity under a high pH condition, it can be seen that a high concentration of buffer under the enzymatic hydrolysis conditions is essential. In this study, 600 mM sodium phosphate buffer, 1 M bicine-NaOH buffer, and 1 M Tris-HCl buffer may be prepared experimentally under hydrolase reaction conditions. For pH capacity, bicine-NaOH buffer and Tris-HCl buffer, which can satisfy high pH conditions, were used. Accordingly, enzymatic hydrolysis was performed under the reaction conditions including 10 g/L of BHET as a substrate, IsPETase$^{Mut}$ enzyme and the IsMHETase$^{Mut}$ enzyme input amounts of 2.3 U/L, a volume of 500 μL, and 1 M bicine-NaOH buffer (pH 8) or 1 M Tris-HCl buffer (pH 8) as a buffer. After the reaction was performed at 40° C. for 6 hours, the samples were diluted in methanol and centrifuged at 25,188 g for 10 minutes, followed by analyzing the supernatant through HPLC. As a result, in FIG. 6h, the result of the reaction under the condition of 1 M bicine-NaOH buffer (pH 8) was confirmed through chromatography, and in FIG. 6I, the result of the reaction under the condition of 1 M Tris-HCl buffer (pH 8) was confirmed through chromatography. After the reaction in FIG. 6h, it can be confirmed that 100% conversion of the substrate BHET to TPA is achieved. However, in the sample after the reaction of FIG. 6i, it was confirmed that an unknown peak, indicating there was no 100% conversion of BHET to TPA, is generated. Therefore, a buffer used in enzymatic hydrolysis was established as 1 M bicine-NaOH buffer (pH 8).

Next, enzymatic hydrolysis was performed under the same conditions as in FIG. 6c, except that 1 M bicine-NaOH buffer (pH 8) was used as a buffer. As a result, in FIG. 6j, it was confirmed that the amounts of the product TPA produced with the enzyme input amounts of 2.3 U/L, 4.5 U/L and 9.0 U/L are similar from 3 hours of reaction. Accordingly, it can be seen that the enzymatic hydrolysis is smoothly performed even when the enzyme input amount relative to the substrate is set to 2.3 U/L, not 9.0 U/L, indicating that wasting of the enzyme may be reduced by using an appropriate input amount of the enzyme. Therefore, the conditions for subsequent enzymatic hydrolysis were established with an enzyme input amount of 2.3 U/L.

To design an efficient and economical process, it is advantageous to obtain a high-concentration and high-yield product through one enzymatic hydrolysis reaction. Therefore, TPA, which is the enzymatic hydrolysis product, was to be obtained at a high concentration in a short time by increasing the concentration of the substrate as much as possible. The reaction conditions included a PET glycolysis product including 10 to 50 g/L of BHET as a substrate, a volume of 500 μL, IsPETase$^{Mut}$ enzyme and the IsMHETase$^{Mut}$ enzyme input amounts of 2.3 U/L, and 1 M bicine-NaOH buffer (pH 8). After the reaction was performed at 40° C. for 12 hours, the samples were diluted in methanol and centrifuged at 25,188 g for 10 minutes, followed by analyzing the supernatant through HPLC. As a result, in FIG. 6k, when the PET glycolysis products including 10 to 40 g/L BHET were used as substrates, the production amount of the product TPA increased, but when the PET glycolysis product including 50 g/L of BHET is used as a substrate, it was confirmed that there is no difference in the production amount of the product TPA from the substrate condition in which the PET glycolysis product includes 40 g/L of BHET at 12 hours after the reaction. Accordingly, when the PET glycolysis product including 50 g/L of BHET was used as a substrate, it can be seen that the condition of the 1 M bicine-NaOH buffer (pH 8) of the enzymatic hydrolysis in the present study cannot buffer the acidity of the produced TPA, so the pH drops and enzyme activity is suppressed.

In FIG. 6l, the yields of 12-hour samples were calculated for each input amount condition of the substrate of FIG. 6k. The left Y axis represents the yield of actually obtained TPA relative to the yield of theoretical TPA compared to initial PET added. The right Y axis represents the yield of actually obtained TPA relative to the yield of theoretical TPA compared to initial BHET added. As a result, when the PET glycolysis product including 50 g/L of BHET was used as a substrate, it was confirmed that the yield decreases significantly compared to the other input amounts of the substrate. Considering the TPA concentrations for each substrate input amount in FIG. 6k and the yields of TPA for each substrate input amount in FIG. 6l, enzymatic hydrolysis was established under the most efficient condition when the substrate input amount was the PET glycolysis product including BHET at a substrate input amount of 40 g/L. Subsequently, as a substrate for whole-cell conversion, which is a biological process, an enzymatic hydrolysate that had been obtained under the above condition was used.

When comparing the left and right Y axes of FIG. 6l, it can be seen that more TPA than the amount of the input BHET is produced as a product. According to this, although the main product of PET glycolysis using betaine as a catalyst is BHET, the part that cannot be measured by liquid chromatography was expected to be an oligomer with a relatively short chain length, not a polymer. To confirm this, enzymatic hydrolysis was performed with various substrates. As substrates, 20 mg of PET granules, 20 mg of a precipitate (oligomer) obtained by washing the PET glycolysis product with distilled water, 40 g/L of BHET, and the PET glycolysis product including 40 g/L of BHET were used. The volume was 500 μL, the input amount of each of the IsPETase$^{Mut}$ enzyme and the IsMHETase$^{Mut}$ enzyme was 2.3 U/L, and 1 M bicine-NaOH buffer (pH 8) was used. After the reaction was performed at 40° C. for 24 hours, the samples were diluted in methanol and centrifuged at 25,188 g for 10 minutes, followed by analyzing the supernatant through HPLC. As a result, in FIG. 6m, it was confirmed that the concentration of the product TPA increases in the order of decreasing polymerization degree (the PET granules>the precipitate (oligomer) obtained by washing the PET glycolysis product with distilled water>BHET>the PET glycolysis product). According to this, it can be seen that the shorter the chain length than the polymer, the faster the reaction rate. In addition, as the TPA production rate of the precipitate (oligomer) obtained by washing the PET glycolysis product with distilled water is higher than that of the PET granules and lower than those of the PET glycolysis product and the BHET, it was experimentally confirmed that, in the product of PET glycolysis using betaine as a catalyst, the part that cannot be measured by liquid chromatography is an oligomer with a relatively short chain length, not a polymer.

<Example 5> Preparation of Strains Capable of Converting Enzymatic Hydrolysate as Substrate into Platform Chemical a of FIG. 7 is the schematic view of a strain that is capable of converting an enzymatic hydrolysate as a substrate into a platform chemical for conversion of TPA into PCA. The TPA-to-PCA conversion is performed in two steps. TPA is first converted into 1,2-dihydroxy-3,5-cyclo-hexadiene-1,4-dicarboxylate (DCD) by the TphAabc enzyme. Here, NAD (P)H acts together, thereby producing NAD(P)$^+$. The DCD is converted into PCA by the TphB enzyme. Here, NAD(P)$^+$ acts together, thereby producing NAD(P)H and CO$_2$. Therefore, to convert TPA into PCA, recombinant plasmids into which the TphAabc gene and TphB gene have been inserted, respectively, have to be transformed into an expression strain. The TphAabc gene was cloned in the pKE112 plasmid. The TphAabc gene and the pKE112 plasmid were cleaved with restriction enzymes KpnI and HindIII, and then ligated to construct pKE112-TphAabc. Likewise, the TphB gene was cloned in the pKM212 plasmid. The TphB gene and the pKM212 plasmid were cleaved with restriction enzymes EcorI and KpnI, and then ligated to construct pKM212-TphB. Both plasmids were transformed into *E. coli* XL1-Blue. The constructed strain is the engineered *E. coli* strain PCA-1 of a of FIG. 7.

d of FIG. 7 is the schematic diagram of converting EG into GLA. The EG-to-GLA conversion proceeds in two steps. EG is first converted into glycolaldehyde using the mADH enzyme. Here, NAD(P)$^+$ acts together, thereby producing NAD(P)H and H$^+$. The glycolaldehyde is converted into GLA using the (m)ALDH enzyme. Here, NAD(P)$^+$ and H$_2$O act together, thereby producing NAD(P)H and H$^+$. *G. oxydans* have various types of polyol dehydrogenases, which can oxidize a wide range of sugars and sugar alcohols. Therefore, to convert EG into GLA, the strain *G. oxydans* (KCCM 40109) was used. This strain is *G oxydans* of d of FIG. 7.

<Example 6> High-Concentration and High-Yield Whole-Cell Conversion of Enzymatic Hydrolysate as Substrate into Platform Chemical PCA was to be produced by whole-cell conversion of an enzymatic hydrolysate using the engineered *E. coli* strain PCA-1, which is the strain constructed as described above, and GLA was to be produced by whole-cell conversion of an enzymatic hydrolysate using *G oxydans*.

First, to produce PCA, the engineered *E. coli* strain PCA-1 was prepared. The preparation process is as follows. The strain was precultured in 5 mL of LB medium containing 50 μg/mL of ampicillin and 40 μg/mL of kanamycin. This was cultured overnight at 37° C. under the condition of 200 rpm. The preculture was inoculated into 1 L of LB medium containing 50 mg/L of ampicillin and 40 mg/L of kanamycin in a 2.8 L flask. This was cultured at 37° C. under the condition of 200 rpm until 600 nm absorbance reached 0.5. At this point, IPTG was inoculated at 0.5 mM and incubated at 16° C. and 200 rpm for 18 hours, inducing gene overexpression of the recombinant plasmid. The gene-over-expressing cells were collected by centrifugation at 4,000 g for 20 minutes at 4° C. The collected cells were washed with 100 mM sodium phosphate buffer (pH 6.5). The collected cells were inoculated into 8 mL of MR medium containing 20 g/L glycerol in a 100 mL flask for whole-cell conversion. The composition of the MR medium consisted of 6.7 g/L of KH$_2$PO$_4$, 4.0 g/L of (NH$_4$)$_2$HPO$_4$, 0.8 g/L of MgSO$_4$-7H$_2$O, 0.8 g/L of citric acid, 10 mg/L of thiamine-HCl, and 5 mL of a trace metal solution. The composition of the trace metal solution consisted of 5.46 g/L of FeSO$_4$, 1.51 g/L of CaCl$_2$, 1.23 g/L of ZnSO$_4$, 0.34 g/L of MnSO$_4$, 0.64 g/L of CuSO$_4$, 0.09 g/L of (NH$_4$)$_6$Mo$_7$O$_{24}$, and 0.01 g/L of Na$_2$B$_4$O$_7$. An enzymatic hydrolysate was added to the reaction medium to have a TPA concentration of 4.5 g/L. In addition, as a positive control, the TPA standard was added to have a concentration of 5.7 g/L under the same conditions. As a result, in b of FIG. 7, a time-dependent trend in TPA reduction and PCA production was confirmed. At 32 hours of whole-cell conversion, it was confirmed that both the whole-cell conversion using the enzymatic hydrolysate as a substrate and the whole-cell conversion using the TPA standard as a substrate were completed. Finally, in the whole-cell conversion using an enzymatic hydrolysate as a substrate, 3.8 g/L of PCA was produced. In c of FIG. 7, the yield is expressed as the number of moles of PCA produced relative to the number of moles of TPA reduced. The *E. coli* PCA-1 strain converted 4.5 g/L TPA in the PET hydrolysate into 3.8 g/L PCA with a molar yield of 90.4% (mol/mol), which is superior to the result of the conversion of reagent-grade TPA into PCA.

Next, to produce GLA, *G oxydans* (KCCM 40109) was prepared. The preparation process is as follows. The strain was precultured in 5 mL of a medium consisting of 20 g/L of sorbitol, 20 g/L of a yeast extract, 5 g/L of (NH$_4$)$_2$SO$_4$, 2 g/L of KH$_2$PO$_4$, and 5 g/L of MgSO$_4$-7H$_2$O. The culture was cultured overnight at 30° C. and 200 rpm. The precul-ture was inoculated into 1 L of the medium under the same conditions in a 2.8 L flask. It was incubated at 30° C. and 200 rpm for 24 hours. Subsequently, the cells were collected by centrifugation at 4,000 g for 20 minutes at 4° C. The collected cells were inoculated into 10 mL of the medium under the same conditions in a 100 mL flask for whole-cell conversion. An enzymatic hydrolysate was added to the reaction medium to have an EG concentration of 30.6 g/L. In addition, as a positive control, the EG standard was added to have a concentration of 34.4 g/L under the same condi-tions. As a result, in b of FIG. 7, a time-dependent trend in EG reduction and GLA production was confirmed. At 21 hours of whole-cell conversion, it was confirmed that the whole-cell conversions using the enzymatic hydrolysate and the EG standard as substrates were completed. Finally, in the whole-cell conversion using the enzymatic hydrolysate as a substrate, 31.4 g/L of GLA was produced. In c of FIG. 7, the yield is expressed as the number of moles of GLA produced relative to the number of moles of EG reduced. When *G oxydans* was used as a whole-cell catalyst, 30.6 g/L of EG in the PET hydrolysate was converted into 31.4 g/L of GLA with a molar yield of 91.6% (mol/mol), which was superior to 90.1% (mol/mol), which is the result of the conversion of reagent-grade EG into GLA. According to this, it was confirmed that it is possible to produce high-concentration and high-yield PCA and GLA from the PET polymer in a chemical-biological integrated process.

TABLE 1

| Comparison of activities of various types of PETase for PET-derived substrate | | | | | | | |
|---|---|---|---|---|---|---|---|
| Substrate | Enzyme | Micro-organism | pH | Temp. (° C.) | Time (h) | Titer of TPA or (sum of TPA, MHET and BHET) | Refer-ence |
| Whole slurry of PET glycolysis | /sPETase$^{S121E/D186H/R280A}$, /sMHETase$^{W397A}$ | *Ideonella sakaiensis* | 8.0 | 40 | 12 | 186.7 mM | This study |
| Oligomers of PET glycolysis oligomers | /sPETase$^{S121E/D186H/R280A}$, /sMHETase$^{W397A}$ | *I. sakaiensis* | 8.0 | 40 | 3 | 9.9 mM | This study |
| PET granule | /sPETase$^{S121E/D186H/R280A}$, /sMHETase$^{W397A}$ | *I. sakaiensis* | 8.0 | 40 | 24 | 61.7 μM | This study |

TABLE 1-continued

Comparison of activities of various types of PETase for PET-derived substrate

| Substrate | Enzyme | Micro-organism | pH | Temp. (° C.) | Time (h) | Titer of TPA or (sum of TPA, MHET and BHET) | Reference |
|---|---|---|---|---|---|---|---|
| PET film | /sPETase$^{Wild}$ | I. sakaiensis | 7.0 | 30 | 18 | (0.3 mM) | Yoshida et al. |
| PET (drinking bottle fabrics) | /sPETase$^{Y58A}$ | I. sakaiensis | 9.0 | 30 | 20 | 21 nM (54.0 nM) | Liu et al. |
| PET film | /sPETase$^{R280A}$ | I. sakaiensis | 9.0 | 30 | 36 | 15.7 µM (31.9 µM) | Joo et al. |
| PET film | /sPETase$^{S121E/D186H/R280A}$ | I. sakaiensis | 9.0 | 40 | 72 | 37.6 µM (120.9 µM) | Son et al. |
| PET coupon | /sPETase$^{W159H/S238F}$ | I. sakaiensis | 7.2 | 30 | 96 | 0.8 mM (1.2 mM) | Austin et al. |
| PET film | /sPETase$^{S214H/I168R/W159H/S188Q/R280A/A180I/G165A/Q119Y/L117F/T140D}$ | I. sakaiensis | 9.0 | 40 | 240 | (3.4 mM) | Cui et al. |
| PET film | /sPETase$^{I179F}$ | I. sakaiensis | 8.5 | 30 | 48 | 6.4 mM | Ma et al. |
| PET film | Hydrolase (TfH) | Thermobifida fusca | 7.0 | 30 | 18 | (<0.1 mM) | Yoshida et al. |
| PET film | Cutinase (LCC) | Leaf-branch compost | 7.0 | 30 | 18 | (<0.1 mM) | Yoshida et al. |
| PET film | Cutinase (FsC) | Fusarium solani | | | | (<0.1 mM) | Yoshida et al. |
| Amorphous PET | Cutinase (FsC) | F. solani | 8.0 | 30 | 96 | 0.9 mM | Vertomme et al. |
| PET fabric | Hydrolase (Tfu$^{Q132A/T101A}$) | T. fusca | 7.5 | 60 | 48 | 19.3 mM | Silva et al. |
| PET flake from a recycling plant | Cutinase (HiC), lipase (CALB) | Humicola insolens, Candida antarctica | 7.0 | 60 to 37[1] | 24 | 13.6 mM | de Castro et al. |
| Amorphous PET | Cutinase (HiC), lipase (CALB) | H. insolens, C. antarctica | 7.0 | 60 to 37[1] | 24 | 60.0 mM | de Castro et al. |

[1]Enzymatic hydrolysis included a reaction at 60° C. with HiC enzyme for 3 hours, and a reaction at 37° C. with a CALB enzyme for 21 hours.

TABLE 2

| catalyst | input PET (g) | temp. (° C.) | EG (g) (or PET/ EG, mol/mol) | catalyst (mg) (or catalyst/PET, wt %) | reaction time (min) | collective yield of of BHET and MHET (%)$^a$ | titer of BHET (g/L) | titer of MHET (g/L) |
|---|---|---|---|---|---|---|---|---|
| betaine | 11.5 | 190 | 11.14 (1:3) | 57.5 (0.5) | 30 | 34.6 | 256.8 | 24.9 |
| | 10.0 | 190 | 12.92 (1:4) | none$^b$ | 30 | 16.8 | 117.1 | N.D.$^c$ |
| | 10.0 | 190 | 12.92 (1:4) | 10.0 (0.1) | 30 | 26.6 | 185.3 | N.D |
| | 10.0 | 190 | 12.92 (1:4) | 50.0 (0.5) | 30 | 52.3 | 330.6 | 27.6 |
| | 10.0 | 190 | 12.92 (1:4) | 100.0 (1) | 30 | 42.4 | 286.9 | 6.8 |
| | 10.0 | 190 | 12.92 (1:4) | 50.0 (0.5) | 60 | 58.7 | 368.6 | 32.8 |
| | 10.0 | 190 | 12.92 (1:4) | 50.0 (0.5) | 90 | 55.1 | 341.2 | 35.1 |
| | 10.0 | 190 | 12.92 (1:4) | 50.0 (0.5) | 120 | 53.8 | 313.8 | 50.4 |
| | 9.0 | 190 | 14.54 (1:5) | 45.0 (0.5) | 30 | 52.7 | 307.6 | 21.6 |
| | 8.0 | 190 | 15.50 (1:6) | 40.0 (0.5) | 30 | 51.6 | 268.3 | 19.1 |
| | 6.0 | 190 | 19.37 (1:10) | 30.0 (0.5) | 30 | 49.8 | 189.8 | 6.7 |
| | 3.5 | 190 | 22.60 (1:20) | 17.5 (0.5) | 30 | 37.2 | 81.3 | 2.9 |
| TBD | 10.0 | 190 | 12.92 (1:4) | 50.0 (0.5)$^d$ | 60 | 55.1 | 328.4 | 45.9 |

$^a$Yield of BHET and MHET = (concentration (g/L) of BHET and MHET) × (total reaction volume (L)/(theoretical maximal content (g) of BHET and MHET from input PET).
$^b$No catalyst was used.
$^c$Not detected.
$^d$TBD was used as a catalyst for glycolysis to compare the catalyst performance of betaine and organic catalysts.

The invention claimed is:

1. A method for depolymerizing polyethylene terephthalate (PET) into an oligomer using glycolysis as a process, with betaine acting as the catalyst.

2. A method of producing a high-value compound from polyethylene terephthalate (PET), comprising:

producing bis(2-hydroxyethyl) terephthalate (BHET) through glycolysis of PET in the presence of betaine as a catalyst;

depolymerizing the produced BHET into terephthalic acid and ethylene glycol via mono(2-hydroxyethyl) terephthalate (MHET) through enzymatic hydrolysis; and converting the terephthalic acid into protocatechuic acid (PCA) through bioconversion in the presence of a biocatalyst, or converting the ethylene glycol into glycolic acid (GLA) through fermentation.

3. The method of claim 1, wherein the glycolysis of PET is performed by applying microwaves in the presence of an ethylene glycol solvent.

4. The method of claim 2, wherein the BHET is hydrolyzed into MHET by IsPETase, and the MHET is hydrolyzed into terephthalic acid and ethylene glycol by IsMHETase.

5. The method of claim 4, wherein the IsPETase consists of the base sequence represented by SEQ ID NO: 1, and the IsMHETase consists of the base sequence represented by SEQ ID NO: 2.

6. The method of claim 2, wherein the bioconversion of terephthalic acid into protocatechuic acid is performed using microorganisms expressing terephthalic acid 1,2-dioxygenase and 1,2-dihydroxy-3,5-cyclohexadiene-1,4-dicarboxylate dehydrogenase as biocatalysts.

7. The method of claim 2, wherein the fermentation of ethylene glycol is performed using ethylene glycol-fermenting microorganisms including one or more selected from the group consisting of *Gluconobacter oxydans* (*G. oxydans*) KCCM 40109, *Clostridium glycolicums*, and *Pseudomonas putida*.

8. The method of claim 2, wherein the glycolysis of PET is performed by applying microwaves in the presence of an ethylene glycol solvent.

\* \* \* \* \*